US012284519B2

United States Patent
Alvarez et al.

(10) Patent No.: US 12,284,519 B2
(45) Date of Patent: Apr. 22, 2025

(54) WIRELESS SETUP AND SECURITY OF A CONTINUOUS ANALYTE SENSOR SYSTEM DEPLOYED IN HEALTHCARE INFRASTRUCTURE

(71) Applicant: Dexcom, Inc., San Diego, CA (US)

(72) Inventors: Aniel Alvarez, Miami, FL (US); Jorge R. Barreras, Dania Beach, FL (US); Reinier Sanchez Bao, Boston, MA (US); Barry Nicholas Solomon, Dania Beach, FL (US); Victor Villaverde Garcia, Dania Beach, FL (US)

(73) Assignee: Dexcom, Inc., San Diego, CA (US)

( * ) Notice: Subject to any disclaimer, the term of this patent is extended or adjusted under 35 U.S.C. 154(b) by 259 days.

(21) Appl. No.: 18/048,818

(22) Filed: Oct. 21, 2022

(65) Prior Publication Data

US 2023/0133145 A1 May 4, 2023

Related U.S. Application Data

(60) Provisional application No. 63/263,560, filed on Nov. 4, 2021.

(51) Int. Cl.
*H04W 12/069* (2021.01)
*A61B 5/00* (2006.01)
(Continued)

(52) U.S. Cl.
CPC .......... *H04W 12/069* (2021.01); *A61B 5/002* (2013.01); *H04L 9/00* (2013.01); *H04L 9/0841* (2013.01);
(Continued)

(58) Field of Classification Search
None
See application file for complete search history.

(56) References Cited

U.S. PATENT DOCUMENTS

| 2013/0042117 A1* | 2/2013 | Birtwhistle | ........... H04W 12/08 713/182 |
| 2017/0308665 A1* | 10/2017 | Heck | ................. A61B 5/14532 |
| 2018/0027412 A1* | 1/2018 | Mandapaka | ...... H04M 1/72412 713/151 |

FOREIGN PATENT DOCUMENTS

WO    2021212516 A1    10/2021

OTHER PUBLICATIONS

International Search Report and Written Opinion for Application No. PCT/US2022/078559 mailed Feb. 13, 2023, 5 pages.

* cited by examiner

*Primary Examiner* — Jeffrey R Swearingen
(74) *Attorney, Agent, or Firm* — Patterson + Sheridan, LLP

(57) ABSTRACT

Techniques and protocols for facilitating wired or wireless secure communications between a sensor system and one or more other devices deployed in healthcare facilities are disclosed. In certain embodiments, the techniques and protocols include secure device pairing techniques and protocols for achieving heightened security, for example, recommended in healthcare facilities. In certain embodiments, a method comprises executing, at an application layer of a sensor system, a password authenticated key exchange (PAKE) protocol with a display device to derive an authentication key; executing, at the sensor system, an authenticated pairing protocol with the display device; after the authenticating is successful, establishing an encrypted connection between the sensor system and the display device; and transmitting, from the sensor system to the display device, analyte data indicative of measured analyte levels via the encrypted connection.

26 Claims, 14 Drawing Sheets

(51) Int. Cl.
  *H04L 9/00* (2022.01)
  *H04L 9/08* (2006.01)
  *H04W 12/03* (2021.01)
  *A61B 5/145* (2006.01)
(52) U.S. Cl.
  CPC ......... *H04W 12/03* (2021.01); *A61B 5/14532* (2013.01)

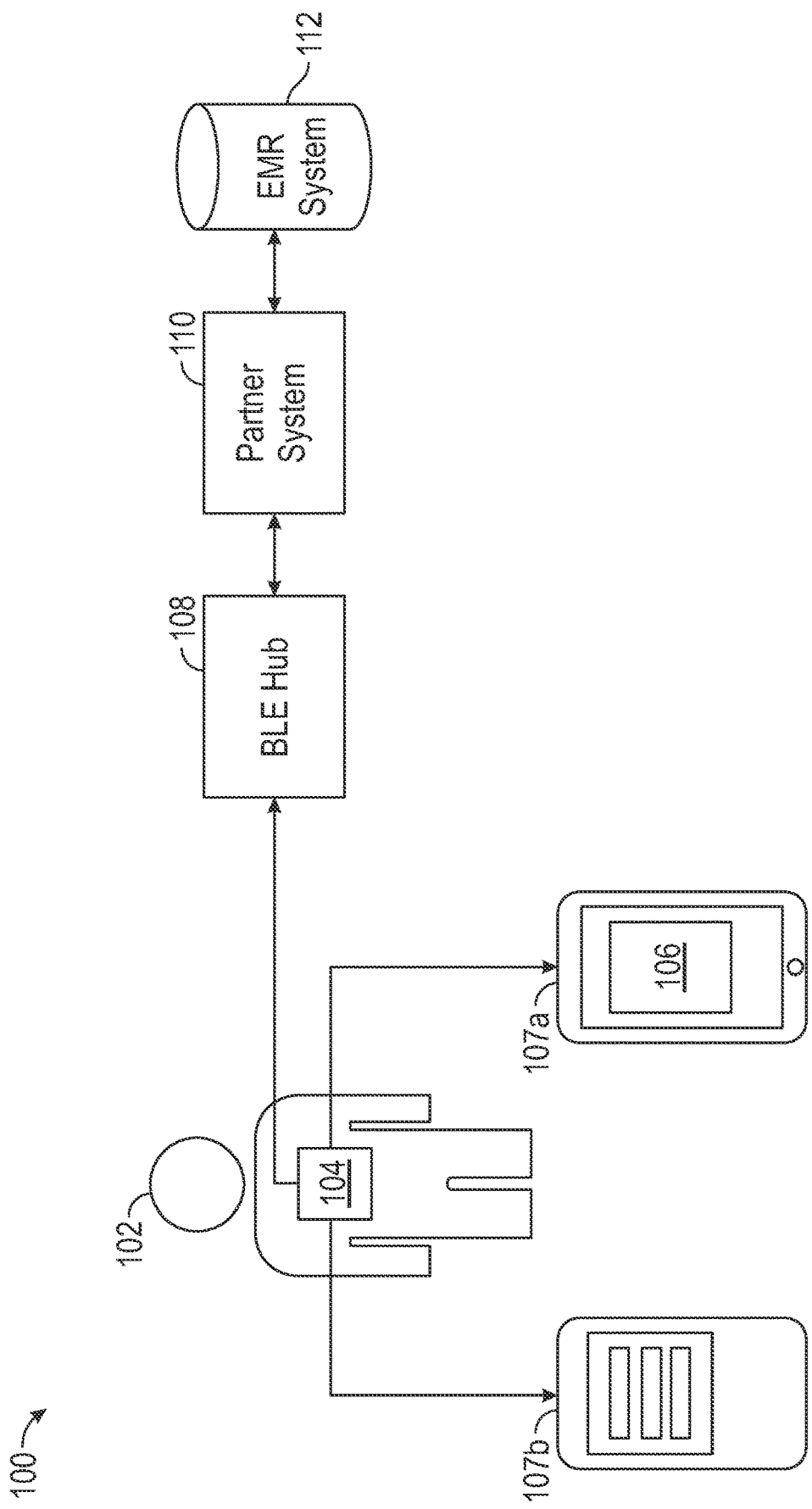

WIRELESS SETUP AND SECURITY OF A CONTINUOUS ANALYTE SENSOR SYSTEM DEPLOYED IN HEALTHCARE INFRASTRUCTURE

CROSS-REFERENCE TO RELATED APPLICATIONS

This application claims priority to and benefit of U.S. Provisional Patent Application No. 63/263,560, filed Nov. 4, 2021, which is hereby assigned to the assignee hereof and hereby expressly incorporated by reference in its entirety as if fully set forth below and for all applicable purposes.

BACKGROUND

The present application relates generally to medical devices such as analyte sensors, and more particularly to systems, devices, and methods related to facilitating wired and wireless secure communications among analyte sensors (e.g., continuous glucose monitoring (CGM) devices), wireless devices, and various wired or wireless nodes in healthcare facilities.

Description of the Related Technology

Diabetes is a metabolic condition relating to the production or use of insulin by the body. Insulin is a hormone that allows the body to use glucose for energy, or store glucose as fat.

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which causes an array of physiological derangements (kidney failure, skin ulcers, or bleeding into the vitreous of the eye) associated with the deterioration of small blood vessels. A hypoglycemic reaction (low blood sugar) may be induced by an inadvertent overdose of insulin, or after a normal dose of insulin or glucose-lowering agent accompanied by extraordinary exercise or insufficient food intake.

Conventionally, a diabetic patient carries a self-monitoring blood glucose (SMBG) monitor, which may require uncomfortable finger pricking methods. Due to the lack of comfort and convenience, a diabetic will normally only measure his or her glucose level two to four times per day. Unfortunately, these time intervals are spread so far apart that the diabetic will likely be alerted to a hyperglycemic or hypoglycemic condition too late, sometimes incurring dangerous side effects as a result. In fact, it is unlikely that a diabetic will take a timely SMBG value, and further the diabetic will not know if his blood glucose value is going up (higher) or down (lower), due to limitations of conventional methods.

Consequently, a variety of non-invasive, transdermal (e.g., transcutaneous) and/or implantable sensors are being developed for continuously detecting and/or quantifying blood glucose values. Generally, in a diabetes management system, these sensors wirelessly transmit raw or minimally processed data for subsequent display and/or analysis at one or more remote devices, which can include a display device, a server, or any other types of communication devices. A remote device, such as a display device, may then utilize a trusted software application (e.g., approved and/or provided by the manufacturer of the sensor), which takes the raw or minimally processed data and provides the user with information about the user's blood glucose levels. Because diabetes management systems using such implantable sensors can provide more up-to-date information to users, they may reduce the risk of a user failing to regulate the user's blood glucose levels.

This background is provided to introduce a brief context for the summary and detailed description that follow. This background is not intended to be an aid in determining the scope of the claimed subject matter nor be viewed as limiting the claimed subject matter to implementations that solve any or all of the disadvantages or problems presented above.

SUMMARY

Certain embodiments of the present disclosure provide a method of facilitating wired or wireless secure communications between a display device and a sensor system for measuring blood glucose levels. The method generally includes executing, at an application layer of the display device, a password authenticated key exchange (PAKE) protocol with the sensor system to derive an authentication key, executing, at the display device, an authenticated pairing protocol with the sensor system, wherein the executing of the authenticated pairing protocol comprises: receiving, at the display device from the sensor system, an indication of a first input/output (I/O) capability configured for the sensor system, wherein the sensor system is not configured with the first I/O capability, obtaining a passkey that is derived based on the authentication key at the application layer of the display device, and authenticating the sensor system by verifying the passkey matches another passkey generated at the sensor system, wherein the other passkey is derived by the sensor system from executing the PAKE protocol at an application layer of the sensor system, after the authenticating is successful, establishing an encrypted connection between the display device and the sensor system, and receiving, at the display device from the sensor system, analyte data indicative of measured analyte levels via the encrypted connection.

Certain embodiments of the present disclosure provide a method of facilitating wired or wireless secure communications between a sensor system for measuring blood glucose levels and a display device. The method generally includes executing, at an application layer of the sensor system, a PAKE protocol with the display device to derive an authentication key, executing, at the sensor system, an authenticated pairing protocol with the display device, wherein the executing of the authenticated pairing protocol comprises: transmitting, from the sensor system to the display device, an indication of a first input/output (I/O) capability configured for the sensor system, wherein the sensor system is not configured with the first I/O capability, obtaining a passkey that is derived based on the authentication key at the application layer of the sensor system, and authenticating the sensor system by verifying that the passkey matches another passkey generated at the display device, wherein the other passkey is derived by the display device from executing the PAKE protocol at an application layer of the display device, after the authenticating is successful, establishing an encrypted connection between the sensor system and the display device, and transmitting, from the sensor system to the display device, analyte data indicative of measured analyte levels via the encrypted connection.

Certain embodiments of the present disclosure provide a sensor system comprising an analyte sensor operable to generate analyte measurements and a sensor electronics module comprising a memory comprising executable instructions and a processor in data communication with the memory and configured to execute the instructions to cause the sensor system to: (i) execute, at an application layer of the sensor system, a password authenticated key exchange (PAKE) protocol with a display device to derive an authentication key; (ii) execute, at the sensor system, an authenticated pairing protocol with the display device, wherein the processor being configured to execute the authenticated pairing protocol comprises the processor being configured to: (1) transmit, from the sensor system to the display device, an indication of a first input/output (I/O) capability, wherein the sensor system is not configured with the first I/O capability; (2) obtain a passkey that is derived based on the authentication key at the application layer of the sensor system; and (3) authenticate the sensor system by verifying that the passkey matches another passkey generated at the display device, wherein the other passkey is derived by the display device from executing the PAKE protocol at an application layer of the display device; (iii) after the authenticating is successful, establish an encrypted connection between the sensor system and the display device; and (iv) transmit, from the sensor system to the display device, analyte data indicative of the analyte measurements via the encrypted connection.

BRIEF DESCRIPTION OF THE DRAWINGS

FIG. 1A illustrates an example health monitoring and support system implemented in hospitals and/or other caregiver facilities (hereinafter "healthcare facilities"), according to some embodiments disclosed herein.

DETAILED DESCRIPTION OF CERTAIN INVENTIVE EMBODIMENTS

Figure 1B:
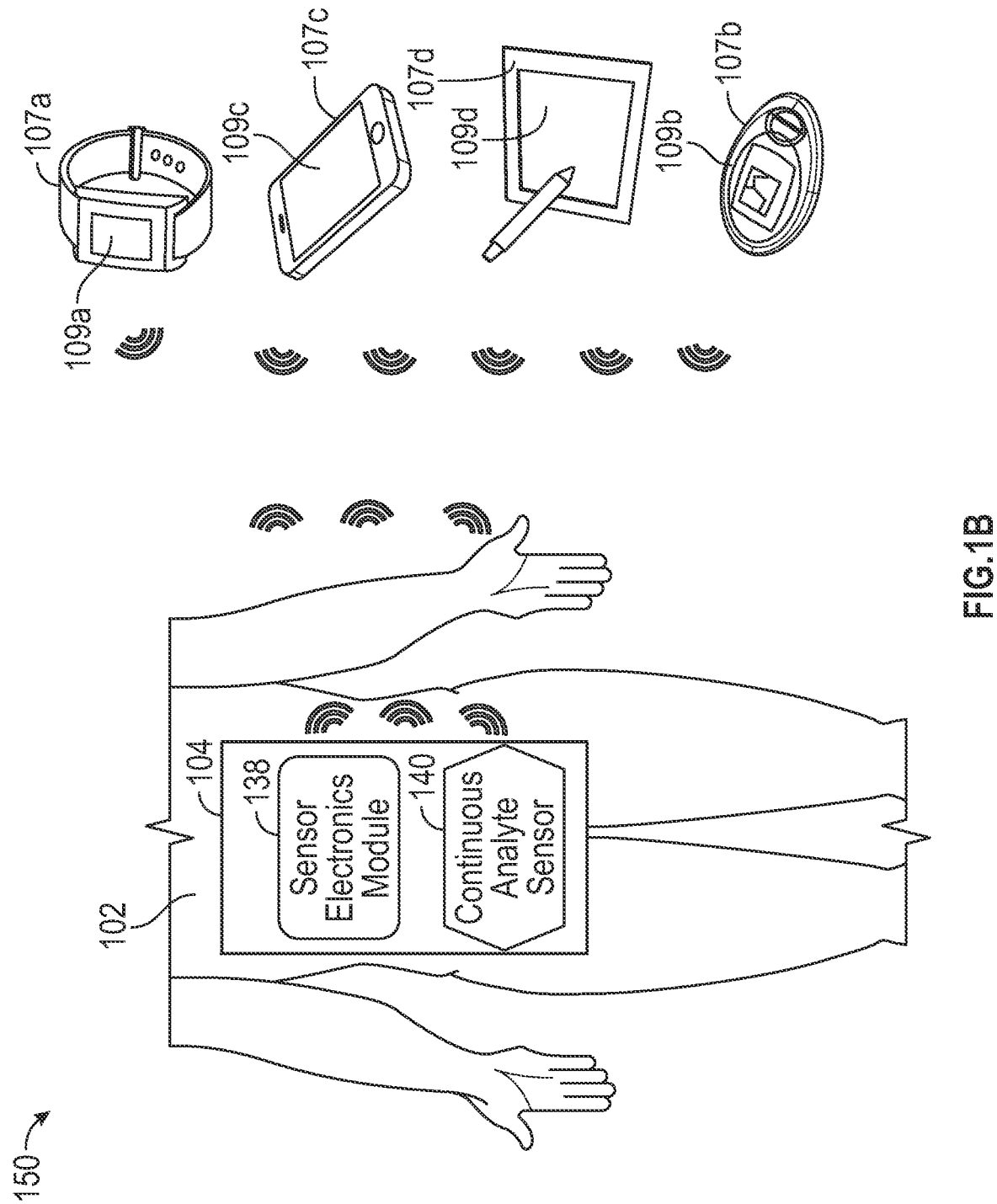
FIG. 1B illustrates the analyte sensor system of FIG. 1A along with a number of display devices 107, according to certain embodiments disclosed herein.

Using a wireless connection between an analyte sensor and one or more remote devices based on certain existing wireless communication protocols, may expose the sensor and/or the remote devices to safety, integrity, privacy, and availability issues (e.g., sensor and/or remote devices may become unavailable as a result of malicious attacks, etc.).

Accordingly, guidelines from governing entities may require stringent security (e.g., cybersecurity) protocols for medical devices to help eliminate such safety, integrity, privacy, and availability issues. In particular, the healthcare industry's accelerating adoption of sophisticated networks, connected devices, and digital records has left modern healthcare facilities acutely vulnerable to cyber-attack. Accordingly, to mitigate the threat to the overall healthcare infrastructure and reduce risks of cyber-attacks, more stringent security protocols may be recommended for use by devices deployed in hospitals and/or other caregiver facilities (referred to herein as "healthcare facilities") to establish more secure wireless connections between these devices as compared to other environments. Stringent security requirements in healthcare facilities are recommended to protect patient safety and privacy, as well as to ensure continuity of effective delivery of high-quality care by mitigating disruptions that can have a negative impact on clinical outcomes.

In one example, to achieve heightened security, devices in healthcare facilities are recommended to engage in authenticated pairing involving a secure exchange of cryptographic keys and, in some cases, in addition to engaging in authenticated pairing, further engaging in a key agreement protocol, such as one involving Elliptic-curve Diffie-Hellman (ECDH) (e.g., Pairing is the process by which two devices exchange device information for purposes of establishing a secure link. The protocol used by the devices for such pairing determines the strength of the authentication associated with the pairing, which directly correlates to the level of security achieved by the devices. Accordingly, devices which engage in authenticated pairing with a password-authenticated key agreement may achieve a higher level of security. For example, using LE Secure pairing may facilitate the protection of the communication from passive eavesdropping regardless of the pairing method used (Passkey Entry, Out Of Band, etc.). Further, authenticated pairing may provide protection from man-in-the-middle (MITM) attacks.

A number of existing protocols exist for achieving authenticated pairing between peer devices (e.g., a pair of devices engaged in the pairing). For example, in some cases, an input/output (I/O)-based pairing method (e.g., a pairing method requiring at least an output capability for one peer device and an input capability for the other peer device), such as a passkey entry protocol, may be used to achieve authenticated pairing. In certain examples, the passkey entry protocol makes use of a multi-digit (e.g., six-digit) passkey (sometimes called a passcode or pairing code) which is accessible to both of the peer devices for authentication. The passkey entry protocol uses a method of gradual disclosure of each bit of the passkey until all bits of the passkey have been verified. The passkey entry method may be used to prevent and/or detect a MITM attack, and further protect the peer devices from passive eavesdropping.

The use of an I/O-based pairing method may be based on I/O capabilities of each of the peer devices. To carry out an I/O-based pairing method like passkey entry pairing, I/O capabilities of one of the peer devices may need to include, at least, a display capability (e.g., monitor, a display, a light emitting diode (LED) display, etc.), while I/O capabilities of the other peer device may need to include, at least, an input capability (e.g., a keyboard, a button, etc.). For example, to verify each bit of a passkey in the passkey entry pairing method, the passkey must first be passed between the peer devices. The way the passkey is passed from one peer device to another may vary. Passkey entry pairing methods may involve the BLE layers of the peer devices (referring to the host and controller components of the BLE protocol stack of the peer devices, as further described below) being configured with instructions to allow one peer device to pass the passkey to the other peer device using the I/O capabilities of the peer devices. For example, in some cases, the BLE layer of a first peer device with at least a display I/O capability causes a random six-digit number to be generated and displayed on the first peer device's display for entry by a user at a second peer device, where the second peer device has at least an input I/O capability. The BLE layer of the second peer device then causes a user interface (UI) feature (e.g., pop-up window or dialogue) to be generated and displayed at the second peer device. The user then reads the number from the display of the first peer device and enters it into the UI feature at the second peer device (e.g., designed with an input capability) using a keypad. Thus, at a minimum, to utilize I/O-based pairing methods, such as passkey entry pairing, at least one of the peer devices needs to have an input capability while the other device would need an output capability to pass the passkey for authentication.

Accordingly, where one or more of the peer devices do not meet the I/O capability requirement (e.g., do not have an input and/or output capability), I/O-based pairing methods may not be feasible where a user is expected to read a key from one peer device and enter the key into the other peer device for authenticated pairing. As such, devices not configured with I/O capabilities suffer from a problem of failing to achieve authenticated pairing using an I/O-based pairing method. As result of this technical problem, such devices may be vulnerable to active and passive eavesdropping and/or MITM attacks. In passive attacks, hackers may intercept and simply monitor information exchanged between the peer devices without altering the information. In active attacks, hackers attempt to modify the integrity and availability of the information they have intercepted with the goal of gaining access or greater privileges.

One or more of the devices deployed in healthcare facilities may be categorized as no input, no output devices. For example, sensors that are provided to patients that are admitted to a hospital and/or a caregiver facility may not be configured with display or keyboard capabilities. As such, deployment of these devices may not allow for meeting recommended security requirements (e.g., at least due to an inability to achieve authenticated pairing) and therefore, adversely impact the security posture of the healthcare facilities.

Accordingly, certain embodiments described herein relate to systems and methods of facilitating wired and wireless secure communications among medical devices, including analyte sensors (e.g., continuous glucose monitoring (CGM) devices), wireless devices, and various wired or wireless nodes, which may not be configured with I/O capabilities. Establishing secure wireless connections using methods described herein may help to reduce safety, integrity, privacy, and/or availability issues associated with wireless communications in the healthcare facilities, thereby improving the security posture of the healthcare facilities.

In certain embodiments, establishing secure wireless communications between an analyte monitoring system and a wireless display device (e.g., receiver, mobile phone, etc.) in healthcare facilities is provided. In particular, authenticated pairing for attaining heightened security, recommended in healthcare facilities, is achieved by using a password authenticated key exchange (PAKE) to generate an authentication key (interchangeably referred to herein as "K-auth") that is used by the peer devices (e.g., the analyte monitoring sensor system and the wireless display device) to derive a passkey for authenticating the connection. Such an implementation removes the need to have two devices with I/O capabilities to achieve authenticated pairing using passkey entry pairing methods.

FIG. 1A depicts a high level system architecture diagram depicting different components of an exemplary healthcare facility implementing a health monitoring and support system 100 (hereinafter "system 100") used for gathering, monitoring, and/or providing information regarding analyte values associated with analytes present in a user's body. In one example, system 100 may be a diabetes management system used for gathering, monitoring, and/or providing information regarding blood glucose levels in a user's body in a healthcare facility. In another example, alternative or in addition to diabetes, system 100 may be used for managing another physiological condition or a combination of conditions by gathering, monitoring, and/or providing information regarding one or more other analytes in the user's body.

The user 102 (hereinafter "the user") of system 100 may be a patient admitted to a hospital and/or other caregiver facility who interacts with a health monitoring device of system 100, such as analyte sensor system 104 (hereinafter "SS 104"). As shown, system 100 includes SS 104, a mobile device 107*a* that executes application 106, a proprietary receiver 107*b* (referred to herein as "receiver 107*b*"), a Bluetooth low energy (BLE) hub 108, an optional partner system 110 (e.g., hospital system, caregiver facility system, or other authorized partner system), and an electronic medical record (EMR) 112.

In certain embodiments, SS 104 is provided for measurement of an analyte in a user. By way of an overview and an example, SS 104 may be implemented as an encapsulated microcontroller that makes sensor measurements, generates analyte data (e.g., by calculating values for continuous monitoring of one or more analytes), and engages in wireless communications to send such data to remote display devices 107, such as mobile device 107*a* and/or receiver 107*b*, authorized partner systems, such as partner system 110, and/or medical delivery devices (e.g., an insulin pump, an infusion pump, etc.).

In certain embodiments, SS 104 and display devices 107 and/or authorized partner systems are configured to wirelessly communicate using low range and/or short distance wireless communication protocols. Further, in certain embodiments, SS 104 and authorized partner systems, such as partner system 110, are configured to wirelessly communicate via a network (e.g., a WiFi network, a BLE network, a wide area network (WAN), the Internet, etc.). Examples of low range and/or short distance wireless communication protocols include Bluetooth and Bluetooth Low Energy (BLE) protocols. In certain embodiments, other short range wireless communications technologies that may be used may include Near Field Communications (NFC), radio frequency identification (RFID) communications, IR (infrared) communications, optical communications. In certain embodiments, wireless communication protocols other than low range and/or short distance wireless communication protocols, such as Wi-Fi Direct, may be used.

Note that, while in certain examples SS 104 is assumed to be a glucose sensor system, SS 104 may operate to monitor one or more additional or alternative analytes. As discussed, the term "analyte" as used herein is a broad term that is to be given its ordinary and customary meaning to a person of ordinary skill in the art (and is not to be limited to a special or customized meaning), and refers without limitation to a substance or chemical constituent in the body or a biological sample (e.g., bodily fluids, including, blood, serum, plasma, interstitial fluid, cerebral spinal fluid, lymph fluid, ocular fluid, saliva, oral fluid, urine, excretions, or exudates). Analytes can include naturally occurring substances, artificial substances, metabolites, and/or reaction products. In some embodiments, the analyte for measurement by the sensing regions, devices, and methods is albumin, alkaline phosphatase, alanine transaminase, aspartate aminotransferase, bilirubin, blood urea nitrogen, calcium, CO2, chloride, creatinine, glucose, gamma-glutamyl transpeptidase, hematocrit, lactate, lactate dehydrogenase, magnesium, oxygen, pH, phosphorus, potassium, sodium, total protein, uric acid, metabolic markers, drugs.

Other analytes are contemplated as well, including but not limited to acetaminophen, dopamine, ephedrine, terbutaline, ascorbate, uric acid, oxygen, d-amino acid oxidase, plasma amine oxidase, xanthine oxidase, NADPH oxidase, alcohol oxidase, alcohol dehydrogenase, pyruvate dehydrogenase, diols, Ros, NO, bilirubin, cholesterol, triglycerides, gentisic acid, ibuprophen, L-Dopa, methyl dopa, salicylates, tetracycline, tolazamide, tolbutamide, acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, glucose-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; glucose-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenyloin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica*, enterovirus, *Giardia duodenalisa, Helicobacter pylori*, hepatitis B virus, herpes virus, HIV-1, IgE (atopic disease), influenza virus, *Leishmania donovani*, leptospira, measles/mumps/rubella, *Mycobacterium leprae, Mycoplasma pneumoniae*, Myoglobin, *Onchocerca volvulus*, parainfluenza virus, *Plasmodium falciparum*, poliovirus, *Pseudomonas aeruginosa*, respiratory syncytial virus, rickettsia (scrub typhus), *Schistosoma mansoni, Toxoplasma gondii, Trepenoma pallidium, Trypanosoma cruzi/rangeli*, vesicular stomatis virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids can also constitute analytes in certain embodiments.

The analyte can be naturally present in the biological fluid, for example, a metabolic product, a hormone, an antigen, an antibody, and the like. Alternatively, the analyte can be introduced into the body, for example, a contrast agent for imaging, a radioisotope, a chemical agent, a fluorocarbon-based synthetic blood, or a drug or pharmaceutical composition, including but not limited to insulin; ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbituates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-dihydroxyphenylacetic acid (DOPAC), homovanillic acid (HVA), 5-hydroxytryptamine (5HT), histamine, Advanced Glycation End Products (AGEs) and 5-hydroxyindoleacetic acid (FHIAA).

With further reference to FIG. 1A, display device(s) in communication with SS 104 may be configured for displaying displayable sensor information that may be transmitted by SS 104 (e.g., in a customized data package that is transmitted to the display devices 107 based on their respective preferences). In certain embodiments, display device(s) 107 in communication with SS 104 may include a custom or proprietary display device, such as receiver 107*b*, which may be an embedded device especially designed for displaying certain types of displayable sensor information associated with analyte data received from SS 104 (e.g., a numerical value and/or an arrow, etc., in certain embodiments).

In certain embodiments, display device(s) 107 in communication with SS 104 may include a mobile device 107*a* based on an Android, iOS, or another operating system (OS). Mobile device 107*a* may be any type of computing device capable of executing an application, such as application 106. Application 106 is a mobile health application that is configured to receive and analyze analyte measurements from SS 104. In particular, application 106 gathers, processes, and displays information about the user, including the user's analyte measurements, and based on the user's analyte measurements, provides alerts, alarms, and/or decision support.

While FIG. 1A illustrates SS 104 in communication with both receiver 107*b* and mobile device 107*a*. In some embodiments, SS 104 is in communication with receiver 107b and not in communication with mobile device 107a and vice versa. In certain embodiments, a mobile device 107a executing application 106 may be an alternative to using a receiver 107b for healthcare facilities that can provide compatible mobile devices 107a and/or prefer the flexibility of a mobile device 107a.

Display devices 107, including mobile device 107a and receiver 107b, may be described in more detail with respect to FIG. 1B.

As mentioned previously, in certain embodiments, SS 104 may engage in wireless communications with one or more authorized partner system(s) (e.g., via Bluetooth and/or other wireless protocols), such as partner system 110 shown in FIG. 1A, to send analyte data to such authorized partner systems. An authorized partner system may be a system that is allowed access to SS 104 for a specific purpose or action. Partner system 110 may include the information technology (IT) infrastructure for an authorized partner made up of hardware and software components, including, facilities, data centers, servers, enterprise application software solutions, etc. Thus, partner system 110 may include the IT infrastructure for a hospital and/or other caregiver facility which includes at least, software components living in the IT infrastructure configured to receive information from SS 104.

As described in more detail below with respect to FIG. 2 and FIG. 3A, to establish a connection with SS 104 so that partner system 110 may receive information from SS 104, partner system 110 may first receive an identification (ID) of SS 104 (e.g., an ID of a transmitter of SS 104) through a router, such as BLE hub 108 (e.g., a BLE/Wi-Fi router). BLE hub 108 allows one or more devices in the healthcare facility (e.g., a computer, a personal device, SS 104) to communicate with partner system 110, with multiple connectivity options. BLE hub 108 may be compatible with the connectivity protocols of the healthcare facility.

In certain embodiments, partner system 110 integrates a certain set of information system standards, such as health level 7 (HL7) health information system (HIS) standards. HL7 provides a framework (and related standards) for the exchange, integration, sharing, and retrieval of electronic health information. These standards define how information is packaged and communicated from one party or device to another, setting the language, structure and data types required for seamless integration between systems and devices In certain embodiments, partner system 110 is connected to an electronic medical record (EMR) system, such as EMR system 112. EMR system 112 is a software platform which allows for the electronic entry, storage, and maintenance of digital medical data. An EMR system is generally used throughout a healthcare facility to document clinical information on patients over long periods. EMR systems organize and present data in ways that assist clinicians with, for example, interpreting health conditions and providing ongoing care, scheduling, billing, and follow up. Data contained in an EMR system may also be used to create reports for clinical care and/or disease management.

As mentioned above, achieving heightened security for healthcare facilities may be technically challenging. For example, stringent security protocols may require authenticated pairing of each of the devices described above, as well as any software application executing thereon. Methods for achieving such authenticated pairing, however, may not be feasible for some medical devices, including SS 104. Accordingly, aspects of the present disclosure provide systems and methods for establishing secure wireless communication between one or more devices and SS 104, which is described in more detail below.

FIG. 1B illustrates an example of SS 104 of FIG. 1A along with a number of display devices 107, according to certain embodiments disclosed herein. In the example of FIG. 1B, SS 104 is a glucose monitoring system. However, as described above, SS 104 may be configured for measuring any other analytes or a combination of multiple analytes.

In certain embodiments, SS 104 includes a sensor electronics module 138 and an analyte sensor 140 associated with sensor electronics module 138. In certain embodiments, sensor electronics module 138 includes electronic circuitry associated with measuring and processing analyte sensor data or information, including algorithms associated with processing and/or calibration of the analyte sensor data/information. Sensor electronics module 138 may be physically/mechanically connected to analyte sensor 140 and can be integral with (i.e., non-releasably attached to) or releasably attachable to analyte sensor 140.

Sensor electronics module 138 may also be electrically coupled to analyte sensor 140, such that the components may be electromechanically coupled to one another (e.g., (a) prior to insertion into a patient's body, or (b) during the insertion into the patient's body). Sensor electronics module 138 may include hardware, firmware, and/or software that enable measurement and/or estimation of levels of the analyte in a user via analyte sensor 140 (e.g., which may be/include a glucose sensor). For example, sensor electronics module 138 can include one or more potentiostats, a power source for providing power to analyte sensor 140, and other components useful for signal processing and data storage, and a telemetry module for transmitting data from the sensor electronics module to one or more display devices 107. Electronics can be affixed to a printed circuit board (PCB) within SS 104, or platform or the like, and can take a variety of forms. For example, the electronics can take the form of an integrated circuit (IC), such as an Application-Specific Integrated Circuit (ASIC), a microcontroller, a processor, and/or a state machine.

Sensor electronics module 138 may include sensor electronics that are configured to process sensor information, such as sensor data, and generate transformed sensor data and displayable sensor information. Examples of systems and methods for processing analyte data are described in more detail herein and in U.S. Pat. Nos. 7,310,544 and 6,931,327 and U.S. Patent Publication Nos. 2005/0043598, 2007/0032706, 2007/0016381, 2008/0033254, 2005/0203360, 2005/0154271, 2005/0192557, 2006/0222566, 2007/0203966 and 2007/0208245, all of which are incorporated herein by reference in their entireties.

Analyte sensor 140 is configured to measure a concentration or level of the analyte in the user. In some embodiments, analyte sensor 140 comprises a continuous glucose sensor, such as a subcutaneous, transdermal (e.g., transcutaneous), or intravascular device. In some embodiments, analyte sensor 140 can analyze a plurality of intermittent blood samples. Analyte sensor 140 can use any method of glucose-measurement, including enzymatic, chemical, physical, electrochemical, spectrophotometric, polarimetric, calorimetric, iontophoretic, radiometric, immunochemical, and the like. Additional details relating to a continuous glucose sensor are provided in paragraphs [0072]-[0076] of U.S. application Ser. No. 13/827,577. Paragraphs [0072]-[0076] of U.S. application Ser. No. 13/827,577 are incorporated herein by reference.

SS 104 may be communicatively coupled to a number of display devices 107, such as mobile devices 107*a*, 107*c*, and 107*d* (individually referred to as mobile device 107*a* and collectively referred to as mobile devices 107*a*) and receiver 107*b*. Note that mobile device 107*a* of FIG. 1A may be any one of mobile devices 107*a*, 107*c*, or 107*d*. In other words, any one of mobile devices 107*a*, 107*c*, or 107*d* may be configured to execute application 106. SS 104 may be communicatively coupled to display devices 107*a*, 107*b*, 107*c*, and/or 107*d*.

Display devices 107 (e.g., mobile device(s) 107*a* and/or receiver 107*b*) may be configured for displaying (and/or providing alerts/alarms based on) displayable sensor information that may be transmitted by sensor electronics module 138 (e.g., in a customized data package that is transmitted to the display devices 107 based on their respective preferences). Each of the mobile devices 107*a*, 107*c*, and/or 107*d* may respectively include a display such as touchscreen display 109*a*, 109*c*, and/or 109*d* for displaying sensor information and/or analyte data to a user and/or receiving inputs from the user. Receiver 107*b* may similarly have a touchscreen display 109*b*. For example, a graphical user interface (GUI) may be presented to the user for such purposes.

In certain embodiments, the display devices 107 may include other types of user interfaces such as voice user interface instead of or in addition to a touchscreen display for communicating sensor information to the user of the display device and/or receiving user inputs. In certain embodiments, one, some, or all of the display devices 107 may be configured to display or otherwise communicate the sensor information as it is communicated from sensor electronics module 138 (e.g., in a data package that is transmitted to respective display devices 107), without any additional prospective processing required for calibration and/or real-time display of the sensor data.

As mentioned herein, receiver 107*b* may be a custom or proprietary device. In some cases, receiver 107*b* may be cleared for inpatient hospital and/or caregiver facility. Receiver 107*b* may be a re-usable display device for use by two or more users, with only one user using receiver 107*b* at a time. In certain embodiments, receiver 107*b* may be initialized and/or reset by a configuration tool. In particular, the configuration tool may be used to load and/or remove the healthcare facility's default settings, set or reset thresholds for alerts and/or alarms configured for the receiver 107*b*, etc.

In certain embodiments, one of the mobile devices 107*a* includes a smartphone, such as mobile phone 107*c*. In certain embodiments, one of the mobile devices 107*a* includes a tablet 107*d*. In certain embodiments, one of the mobile devices 107*a* includes a smartwatch 107*a*. Each of these mobiles devices 107*a* may be based on an Android, iOS, or another OS for executing various software applications, such as application 106.

In certain embodiments, sensor electronics module 138 may be configured to transmit sensor information and/or analyte data to a medical delivery device (e.g., an insulin pump or pen). The medical delivery device (not shown) may be configured to administer a certain dosage of insulin or another medicament to the user based on the sensor information and/or analyte data (e.g., which may include a recommended insulin dosage) received from the sensor electronics module 138 as well as indications or treatment recommendations received from mobile device 107*a* or receiver 107*b*.

Figure 1C:
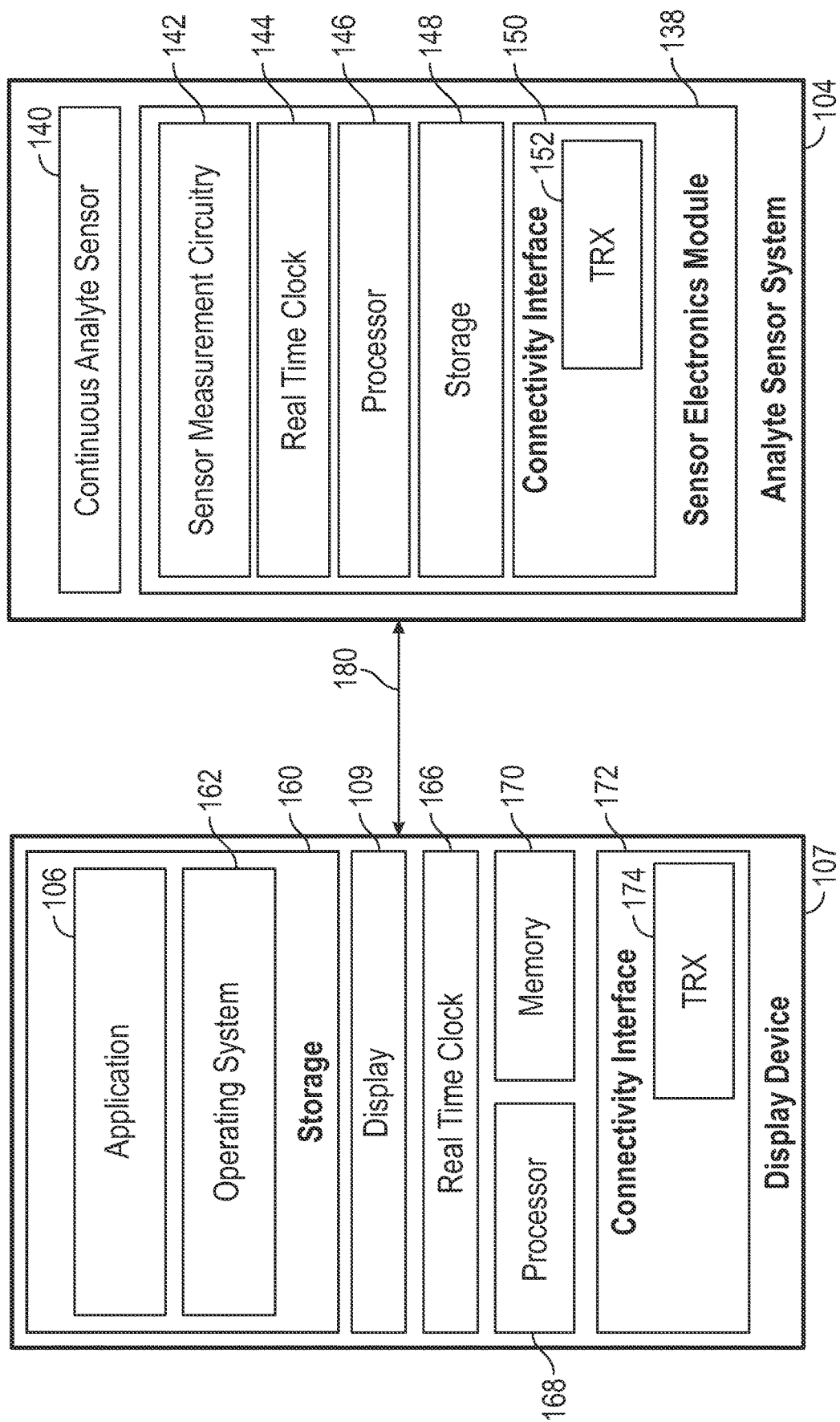
FIG. 1C illustrates the analyte sensor system and display device of FIGS. 1A and 1B, in more detail, according to certain embodiments disclosed herein.

FIG. 1C illustrates example components of SS 104 and display device 107 (e.g., mobile device 107*a* and/or receiver 107*b*, of FIGS. 1A and 1B) in more detail, according to certain embodiments disclosed herein. As mentioned previously, in certain embodiments, SS 104 includes analyte sensor 140 coupled to sensor electronics module 138. Sensor electronics module 138 includes sensor measurement circuitry 142 that is coupled to analyte sensor 140 for processing and managing sensor data. Sensor measurement circuitry 142 may also be coupled to processor 146. In some embodiments, processor 146 may perform part or all of the functions of the sensor measurement circuitry 142 for obtaining and processing sensor measurement values from analyte sensor 140. Processor 146 may also be coupled to storage 148 and real time clock (RTC) 144 for storing and tracking sensor data. In addition, processor 146 may be further coupled to a connectivity interface 150, which includes a radio unit or transceiver (TRX) 152 (also referred to herein as a "transmitter") for sending sensor data and receiving requests and commands from a remote display device 107. As used herein, the term transceiver generally refers to a device or a collection of devices that enable SS 104 to (e.g., wirelessly) transmit and receive data. SS 104 may further include storage 148 and real time clock (RTC) 144 for storing and tracking sensor data. It is contemplated that, in some embodiments, sensor measurement circuitry 142 may carry out all the functions of processor 146 and vice versa.

Transceiver 152 may be configured with the necessary hardware and wireless communications protocols for enabling wireless communications between SS 104 and other remote devices, such as display device 107 and/or partner system 110. For example, as described above, transceiver 152 may be configured with the necessary hardware and communication protocols to establish a Bluetooth or BLE connection with display device 107. As one of ordinary skill in the art appreciates, in such an example, the necessary hardware may include a Bluetooth or BLE security manager and/or other Bluetooth or BLE related hardware/software modules configured for Bluetooth or BLE communications standards.

Further, as shown in FIG. 1C, display device 107 includes connectivity interface 172, processor 168, memory 170, an RTC 166, a display 109 for presenting a graphical user interface (GUI), and a storage 160. A bus (not shown) may be used to interconnect the various elements of the display device and transfer data between these elements. Connectivity interface 172 includes a transceiver (TRX) 174 used for receiving sensor data from SS 104. Transceiver 174 is coupled to other elements of display device 107 via connectivity interface 172 and/or the bus. Transceiver 174 may include multiple transceiver modules operable on different wireless standards. For example, transceiver 174 may be configured with one or more communication protocols, such as wireless communication protocol(s) for establishing a wireless communication path with a network and/or low range wireless communication protocol(s) (e.g., Bluetooth or BLE) for establishing a wireless communication path with SS 104.

In some embodiments, when a standardized communication protocol is used between the display device 107 and SS 104, commercially available transceiver circuits may be utilized that incorporate processing circuitry to handle low level data communication functions such as the management of data encoding, transmission frequencies, handshake protocols, security, and the like. In such embodiments, processor 168 of the display device and/or processor 146 of SS 104 may not need to manage these activities, but instead provide desired data values for transmission, and manage high level functions such as power up or down, set a rate at which messages are transmitted, and the like. Instructions and data values for performing these high level functions can be provided to the transceiver circuits via a data bus and transfer protocol established by the manufacturer of transceivers 174 and 152.

Processor 168 may include processor sub-modules, including, by way of example, an applications processor that interfaces with and/or controls other elements of the display device (e.g., connectivity interface 172, application 106, display 109, RTC 166, memory 170, storage 160, etc.). In certain embodiments, processor 168 is configured to perform functions related to device management, such as, for example, managing lists of available or previously paired devices, information related to network conditions (e.g., link quality and the like), information related to the timing, type, and/or structure of messaging exchanged between SS 104 and display device 107, and so on. Processor 168 may further be configured to receive and process user input as well as analyte data. In certain embodiments, processor 168 may access stored content from storage 160 and memory 170 at the direction of application 106, and process the stored content to be displayed by display 109. Additionally, processor 168 may process the stored content for transmission via connectivity interface 172 to SS 104. Display device 107 may include other components not shown in detail in FIG. 1C.

In certain embodiments, memory 170 may include volatile memory, such as random access memory (RAM) for storing data and/or instructions for software programs and applications, such as analyte sensor application 106. Display 109 is configured to present a GUI associated with OS 162 and/or application 106. In various embodiments, a user may interact with application 106 via a corresponding GUI presented on display 109.

As mentioned previously, application 106 may process and/or present analyte-related data received by display device 107 and present such data via display 109. Additionally, application 106 may be used to interface with SS 104, which includes obtaining analyte data generated by SS 104, as is described in further detail herein.

Storage 160 may be a non-volatile storage for storing software programs, instructions, data, etc. For example, storage 160 may store application 106 that, when executed using processor 168, for example, receives input (e.g., by a conventional hard/soft key or a touch screen, voice detection, or other input mechanism), allows a user to interact with the analyte data and related content via display 109, etc. Storage 160 may further be used to store volumes of analyte data received from at least SS 104 for later retrieval and use, e.g., for determining trends and triggering alerts.

As mentioned previously, SS 104, in certain embodiments, gathers analyte data from analyte sensor 140 and transmits the same or a modified version of the collected data to display device 107. Data points regarding analyte values may be gathered and transmitted over the life of analyte sensor 140 (e.g., in the range of 1 to 30 days or more). New measurements may be transmitted often enough to adequately monitor analyte levels of a user of SS 104. In certain embodiments, rather than having the transmission and receiving circuitry of each of SS 104 and display device 107 continuously communicate, SS 104 and display device 107 may regularly and/or periodically establish a communication channel among each other. Thus, in such embodiments, SS 104 may, for example, communicate with display device 107 at predetermined time intervals. The duration of the predetermined time interval can be selected to be long enough so that SS 104 does not consume too much power by transmitting data more frequently than needed, yet frequent enough to provide substantially real-time sensor information (e.g., measured glucose values or analyte data) to the display device for output (e.g., via display 109) to the user. This time interval can be varied to be any desired length of time. In other embodiments, transceivers 152 and 174 may be continuously communicating. For example, in certain embodiments, transceivers 152 and 174 may establish a session or connection there between and continue to communicate together until the connection is lost.

In order for display device 107 to interface with SS 104, a user (e.g., a staff member at a healthcare facility) may be directed by application 106 to wirelessly connect display device 107 to a patient's SS 104, which may have already been placed on the patient's body (e.g., by a healthcare professional, such as a nurse, nurse administrator, etc.). A wireless communication path 180 between display device 107 and SS 104 allows SS 104 to transmit analyte measurements to display device 107 and for the two devices to engage in any of the other interactions described above.

A number of protocols may be used by display device 107 and SS 104 to establish a secure connection, thereby, reducing safety, integrity, privacy, and availability issues associated with communications in system 100. Different protocols may be used by display device 107 and SS 104 to achieve different levels of security (e.g., having different levels of vulnerability to attack).

As mentioned previously, to improve the security posture of healthcare facilities, heightened security protocols for preventing cyber threats are recommended. In particular, more stringent security protocols, often requiring authenticated pairing, may be recommended for use by display device 107 and SS 104 to establish such a connection in healthcare facilities as compared to other environments. Stringent security protocols, often requiring authenticated pairing, may also be recommended for establishing secure connections between SS 104 and other devices in the healthcare facility.

In certain embodiments, display device 107 is designed with both input and output capabilities, while SS 104 (and more specifically, a transmitter of SS 104) is designed to have an input capability, an output capability, and/or both an input and output capability to be able to perform passkey entry pairing methods for achieving authenticated pairing. For example, as discussed above, display device 107 and SS 104 are configured (e.g., at the BLE layer) to engage in passkey entry pairing methods, involving one of either the display device or SS 104 generating a random passkey while the other having input capabilities for the user to input the passkey.

In certain other embodiments, display device 107 is designed with input and/or output capabilities, while SS 104 is designed to have no input and/or output capabilities. As mentioned herein, in certain embodiments, SS 104 includes an embedded transceiver in sensor electronics module 138 which may not be designed with a display or a keyboard. Accordingly, in such embodiments, performing an I/O-based pairing method may not be possible where a user is expected to read a key from one peer device and enter the key into the other peer device for authenticated pairing. Thus, to establish secure wireless communications between SS 104 and display device 107, certain aspects described herein involve various methods for achieving authenticated pairing using a passkey that is derived at the application layer. For example, in certain aspects, SS 104 and display device 107 may achieve authenticated pairing using an application layer passkey that is derived based on an authentication key (i.e., K-auth) generated, at the application layer, as a result of the peer devices executing a key exchange protocol, such as PAKE. In certain embodiments, the application layer passkey may then be passed to the BLE layer (described in more detail below) at each peer device. Once both peer devices are in possession of the same passkey, at the BLE layer, the peer devices are able to proceed with and achieve authenticated pairing using the passkey. Therefore, by using K-auth to derive a passkey which is passed to a BLE layer of each peer device, the need for I/O capability at both peer devices may be circumvented.

PAKE or similar key exchange protocols are designed to allow two peer devices (e.g., display device 107 and SS 104) to generate or derive, the application layer, a high entropy authentication key (e.g., K-auth) from a shared low entropy secret. As used herein, the application layer of a peer device refers to an abstraction layer or service that specifies the shared protocols (e.g., communication protocols, identification protocols, authentication protocols, etc.) and interface methods used for communication with other devices. For example, within the Open Systems Interconnect (OSI) standard reference model, the application layer is the highest layer for managing communications between applications on devices. In BLE enabled devices, the functionality of the BLE protocol stack, as defined by the Bluetooth® Special Interest Group (SIG), is divided between three main layers, e.g., the application, the controller, and the host, where each layer is designed to perform various different functions. In the BLE protocol stack, the application layer is the direct user interface defining profiles that afford interoperability between various applications. The other two components of the BLE protocol stack, i.e., the controller and the host, are collectively referred to as the BLE layer. The controller component includes the BLE PHY (physical), the LL (link layer), and the Controller-Side Host Controller Interface (HCl). The BLE PHY air interface operates in the same unlicensed 2.4 GHz Industrial, Scientific, and Medical (ISM) frequency band as Wi-Fi®. The LL performs tasks similar to the medium access control (MAC) layer of the OSI model. The Controller-Side HCl handles the interface between the host and the controller.

The host component includes a Host-Side HCl, Logical Link Control and Adaptation Protocol (L2CAP), Attribute Protocol (ATT), Generic Attributed Profile (GATT), Security Management Protocol (SMP), and Generic Access Profile (GAP). The Host-Side HCl handles the interface between the host and the controller. The L2CAP encapsulates data from the BLE higher layers into the standard BLE packet format for transmission or extracts data from the standard BLE LL packet on reception according to the link configuration specified at the ATT and SMP layers. The ATT transfers attribute data between clients and servers in GATT-based profiles. The GATT provides a reference framework for all GATT-based profiles. The SMP applies security algorithms to encrypt and decrypt data packets. The GAP specifies roles, modes, and procedures of a device. The application layer communicates directly with the GAP of the host component.

As discussed, in certain embodiments, the two peer devices (e.g., display device 107 and SS 104) may be configured at the application layer to engage in a key exchange protocol, such as PAKE, to derive a passkey for authenticating the connection. In order to authenticate the connection between the two peer devices, the two devices may engage, at the BLE layer, in passkey entry pairing using the derived passkey. However, for certain display devices 107, including mobile devices 107a, such as smart phones, with commercially available OSs, passing the passkey from the application layer to the BLE layer may be technically challenging. Accordingly, as discussed in more detail below, certain aspects described herein relate to various methods for passing the passkey derived at the application layer to the BLE layer at commercially available mobile devices 107a such that authenticated pairing may be performed and completed at the BLE later.

Further, as part of an I/O-based pairing method, such as passkey entry pairing, initially each peer device may be required to disclose its I/O capabilities. The I/O capabilities disclosed between the peer devices may then help determine whether an I/O-based pairing method can be used to achieve authenticated pairing. Accordingly, given that in certain embodiments, SS 104 has neither an input nor an output capability, if SS 104 reports no I/O capabilities to display device 107, the peer devices may determine that passkey entry pairing may not be a feasible option. For this reason, in order to ensure that SS 104 and display device 107 proceed with the pairing process, SS 104 may be configured to report fake I/O capabilities to display device 107 to trigger execution of the passkey entry pairing protocol in certain embodiments.

For example, in certain embodiments, SS 104 may be configured to report a fake output/display capability to mobile device 107a (e.g., a mobile device with a commercially available OS), thereby causing mobile device 107a to skip generating a random passkey, since mobile device 107a may be configured (per its BLE configuration) to generate a random passkey when a SS 104 reports input only capabilities or no capabilities. More particularly, instead of disclosing its real capabilities (e.g., no I/O capabilities), SS 104 may be configured to report to mobile device 107a that SS 104 has output/display capabilities. Reporting of sham output/display capabilities would cause mobile device 107a to refrain from generating a random passkey for pairing, and instead, allow SS 104 to generate a passkey at the application layer. SS 104 may be programmed to report such sham capabilities as well as generate an application layer passkey for pairing. SS 104 and mobile device 107a may pass the passkey derived at the application layer, e.g., using methods described herein, to perform the I/O-based pairing method.

In certain embodiments, SS 104 may be configured to report different fake I/O capabilities when pairing with mobile device 107a than when pairing with receiver 107b such that, in cases where SS 104 is pairing with both of mobile device 107a and receiver 107b, SS 104 may be able to distinguish the two connections or pairing sessions. Accordingly, in certain embodiments, SS 104 may be configured to report a fake input capability to receiver 107b (and report a fake output capability to mobile device 107a, as describe above). Receiver 107b may be programmed to derive the passkey at the application layer and allow for passing of the passkey to the BLE layer where the passkey is then used for authentication.

Methods for reporting fake I/O capabilities and passing of the passkey to the BLE layer to allow for authenticated pairing between peer devices may be described in more detail below with respect to, at least, FIGS. 4 and 5.

Figure 2:
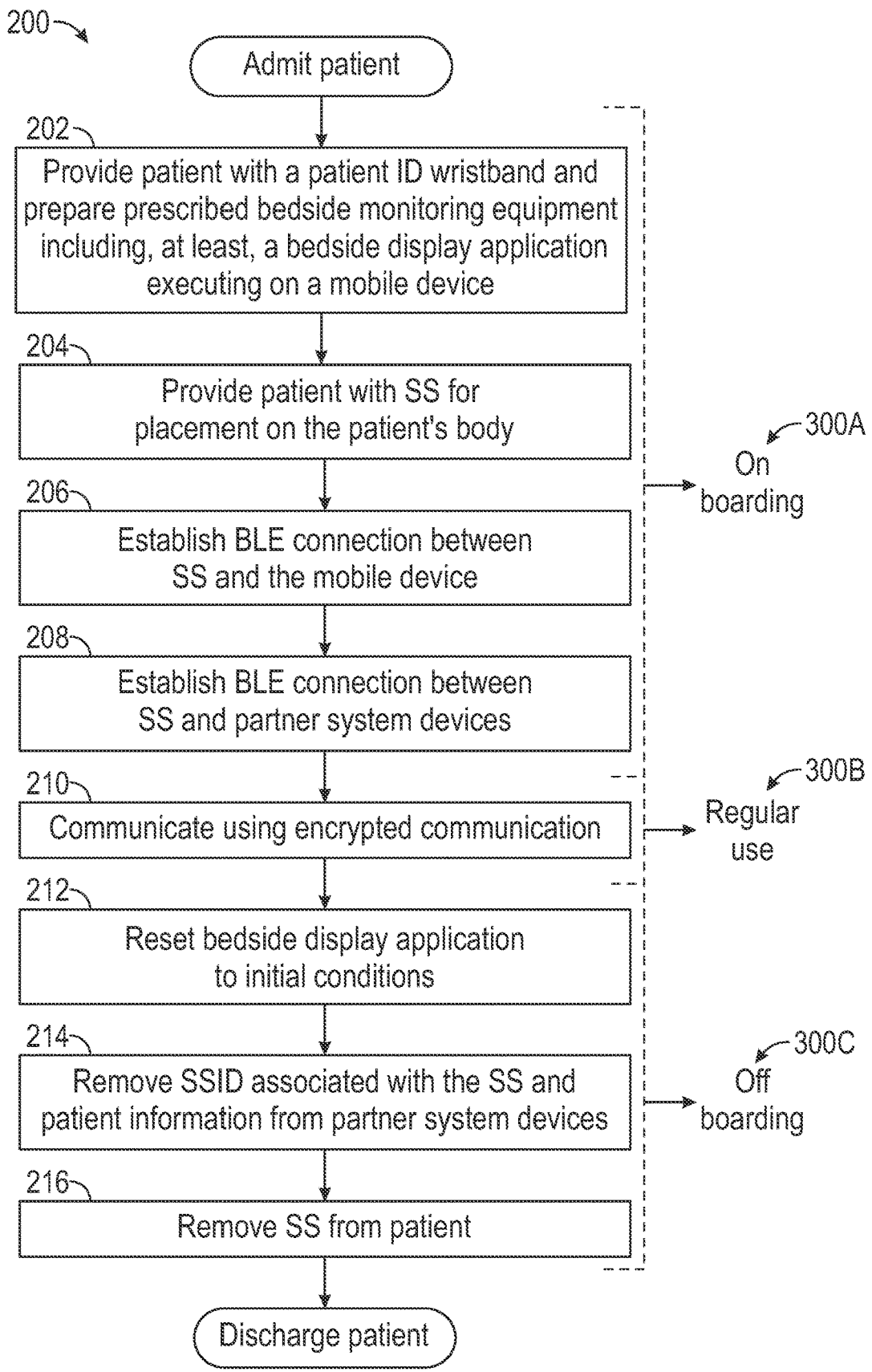
FIG. 2 is a flow diagram illustrating example operations for establishing secure wireless connections between devices deployed in healthcare facilities, according to certain embodiments disclosed herein.

Specifically, FIG. 2 is a flow diagram illustrating example operations for establishing secure wireless connections between devices deployed in an example healthcare facility. FIGS. 3A-3C provide example illustrations of the operations described in FIG. 2 for the on boarding and off boarding of devices in the healthcare facility. FIGS. 4 and 5 are sequence diagrams illustrating communications and exchange of data between SS 104 and mobile device 107a. More specifically, FIG. 4 relates to the execution of security protocols for establishing secure wireless communications between SS 104 and mobile device 107*a* having a first OS (e.g., where passing of the passkey from the application layer to the BLE layer of mobile device 107*a* is not restricted). FIG. 5 relates to the execution of security protocols for establishing secure wireless communications between SS 104 and mobile device 107*a* having a second OS (e.g., where passing of the passkey from the application layer to the BLE layer of mobile device 107*a* is restricted).

On Boarding and Off Boarding Procedures for Devices Deployed in a Healthcare Facility Deploying medical devices, including analyte sensors such as SS 104, wireless display devices 107 such as receivers 107*b* and/or mobile devices 107*a*, and various wired or wireless nodes in healthcare facilities may involve initial setup and reset of such devices each time a new patient is admitted and discharged. For example, such devices may be considered short-term use devices as they are normally intended for continuous use by a patient for acute patient care (e.g., continuous use of the device for between 60 minutes to 30 days) and are further intended by a manufacturer of the device to be reused by a future patient after appropriate procedures such as cleaning, disinfection, sterilization, and/or information resetting have been carried out.

Figure 3A:
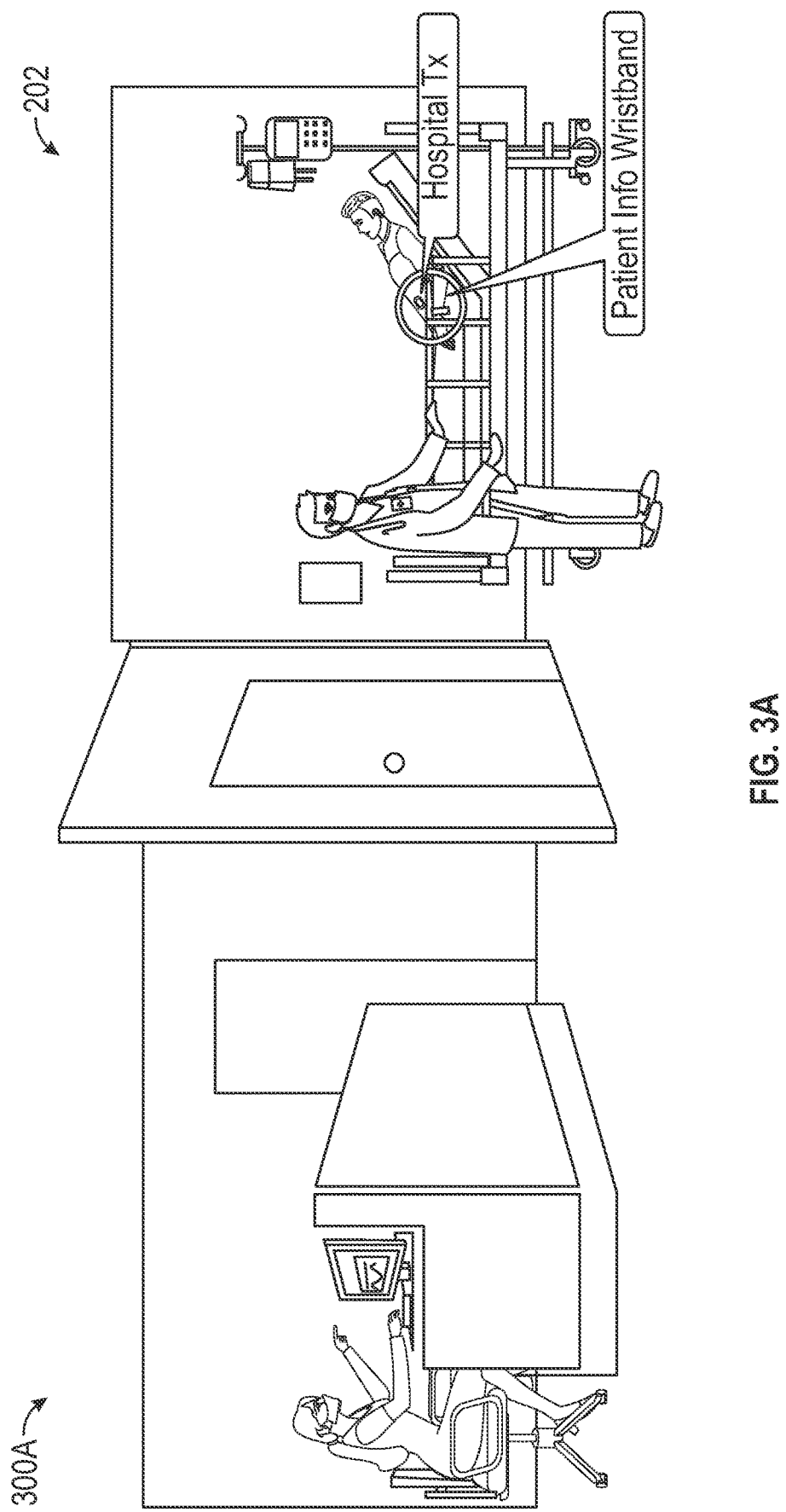
FIGS. 3A-3C provide example illustrations of the operations described in FIG. 2 for the on boarding, regular use, and off boarding of devices in healthcare facilities, according to certain embodiments disclosed herein.
Figure 3A:
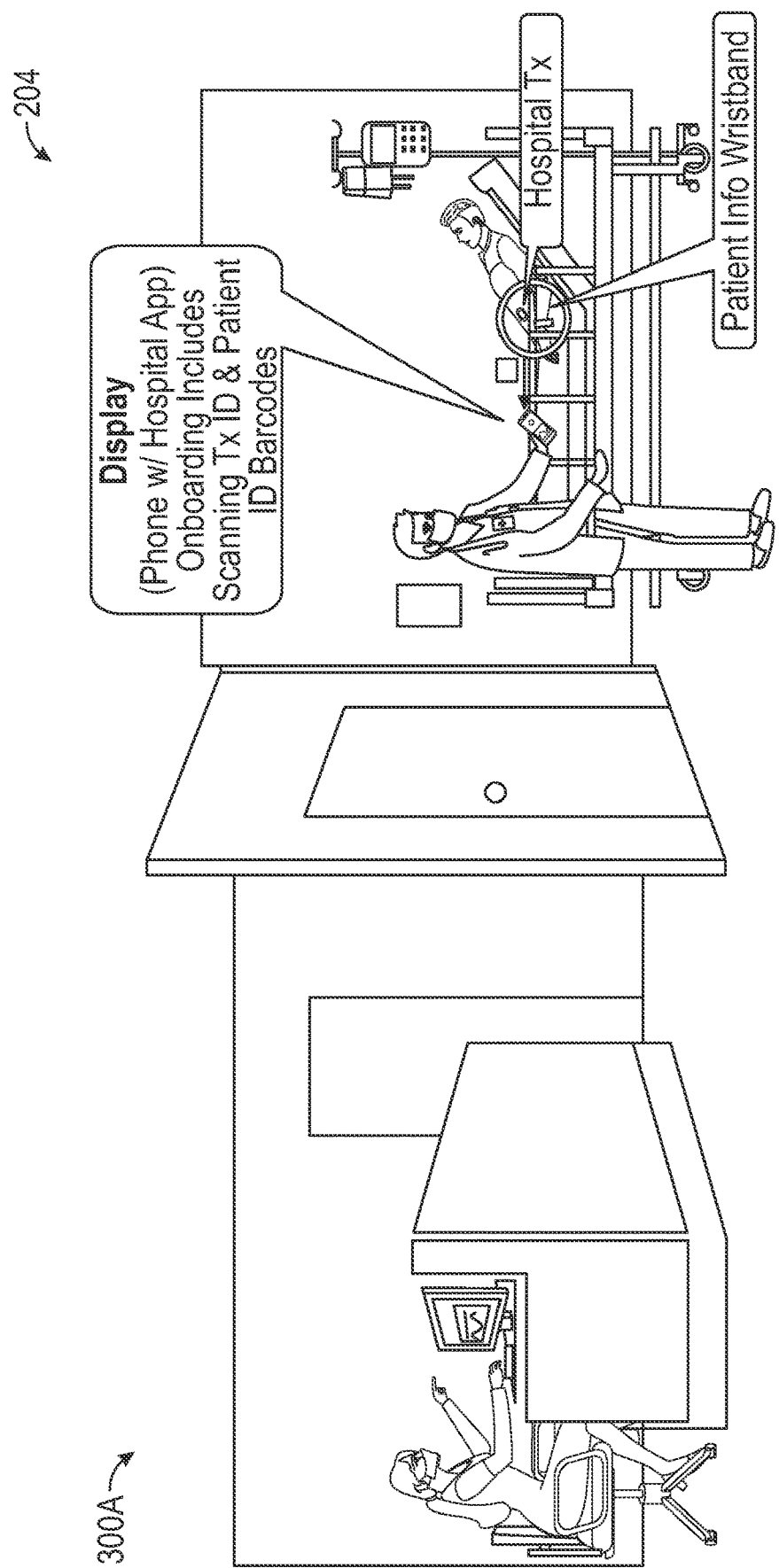
Figure 3A:
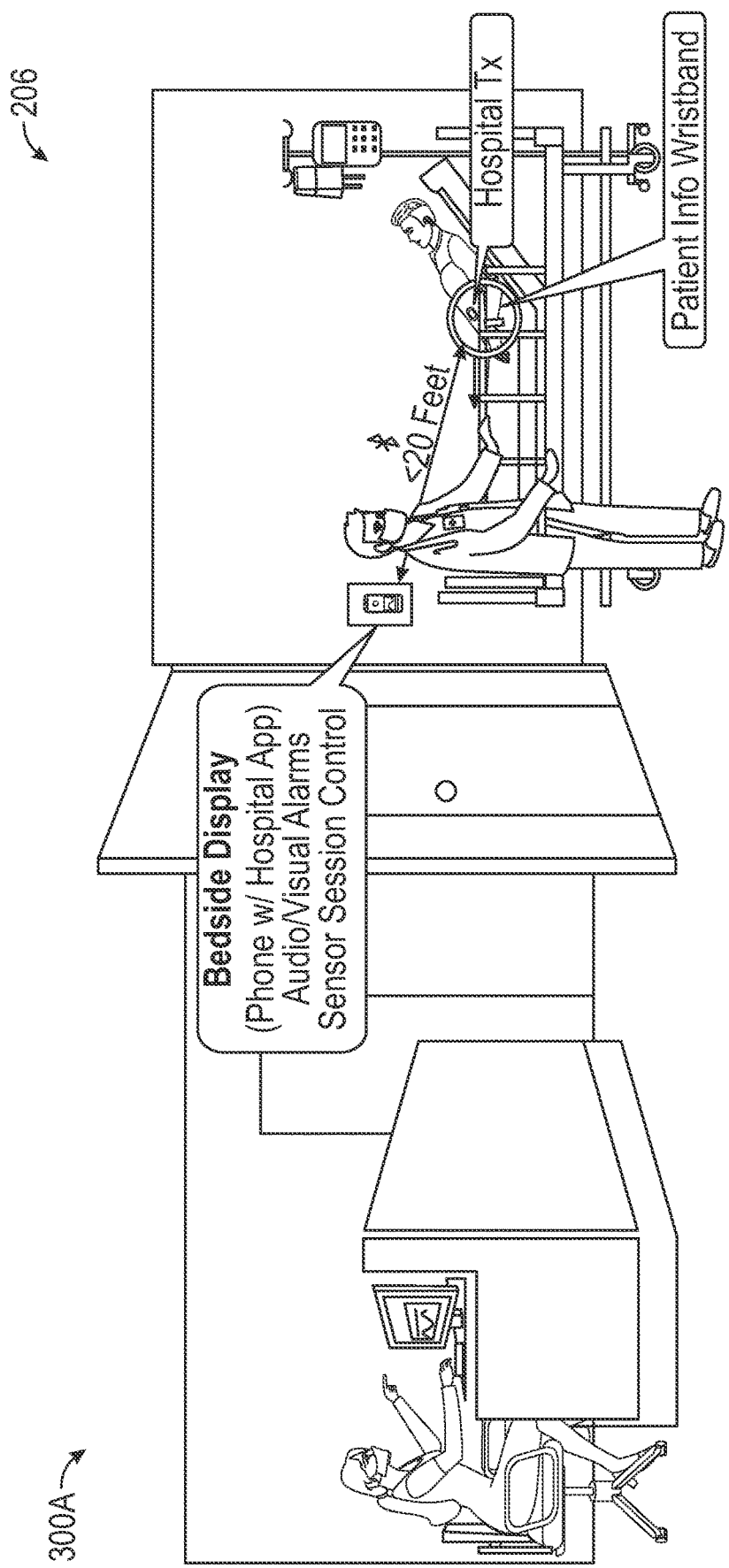
Figure 3A:
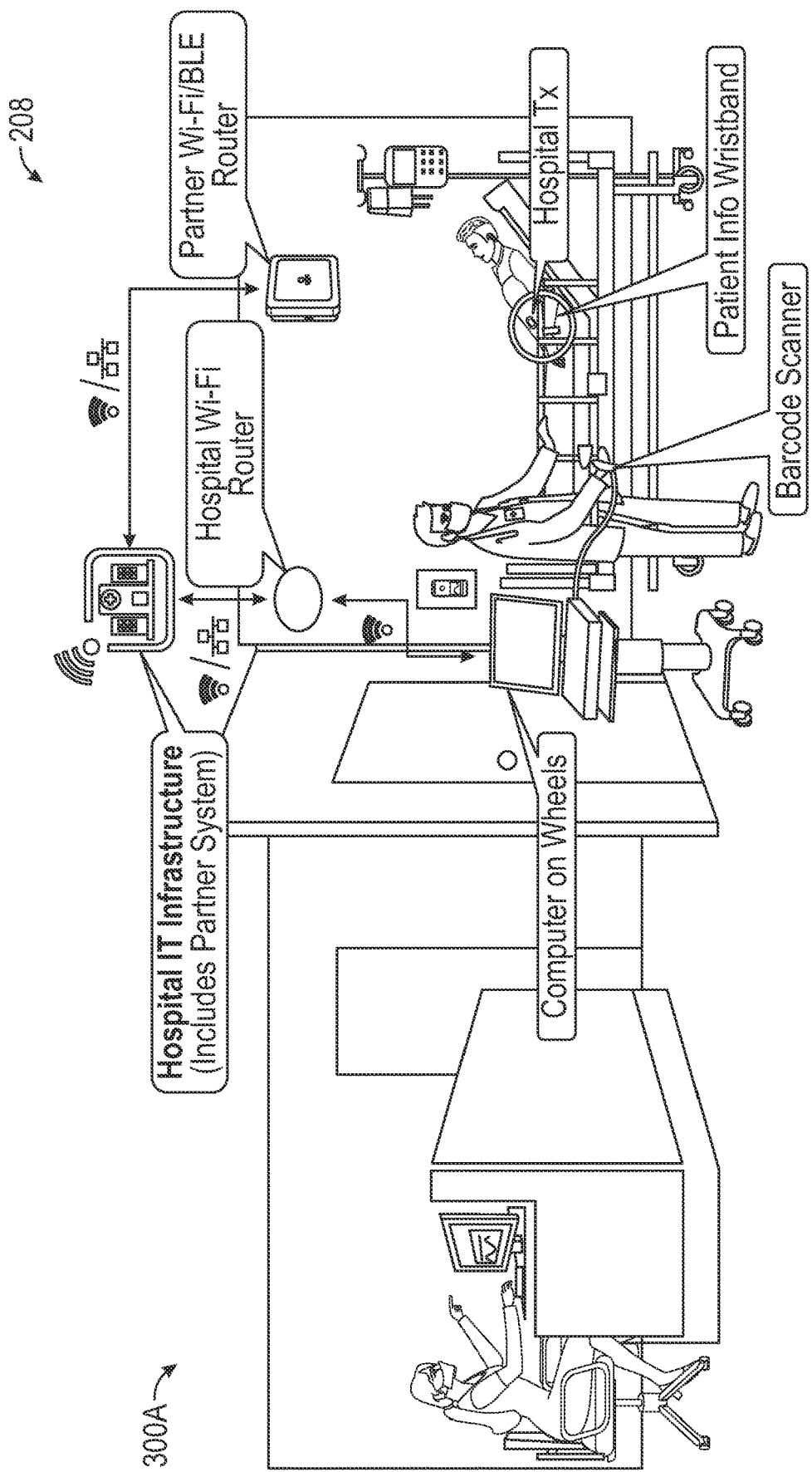
Figure 3B:
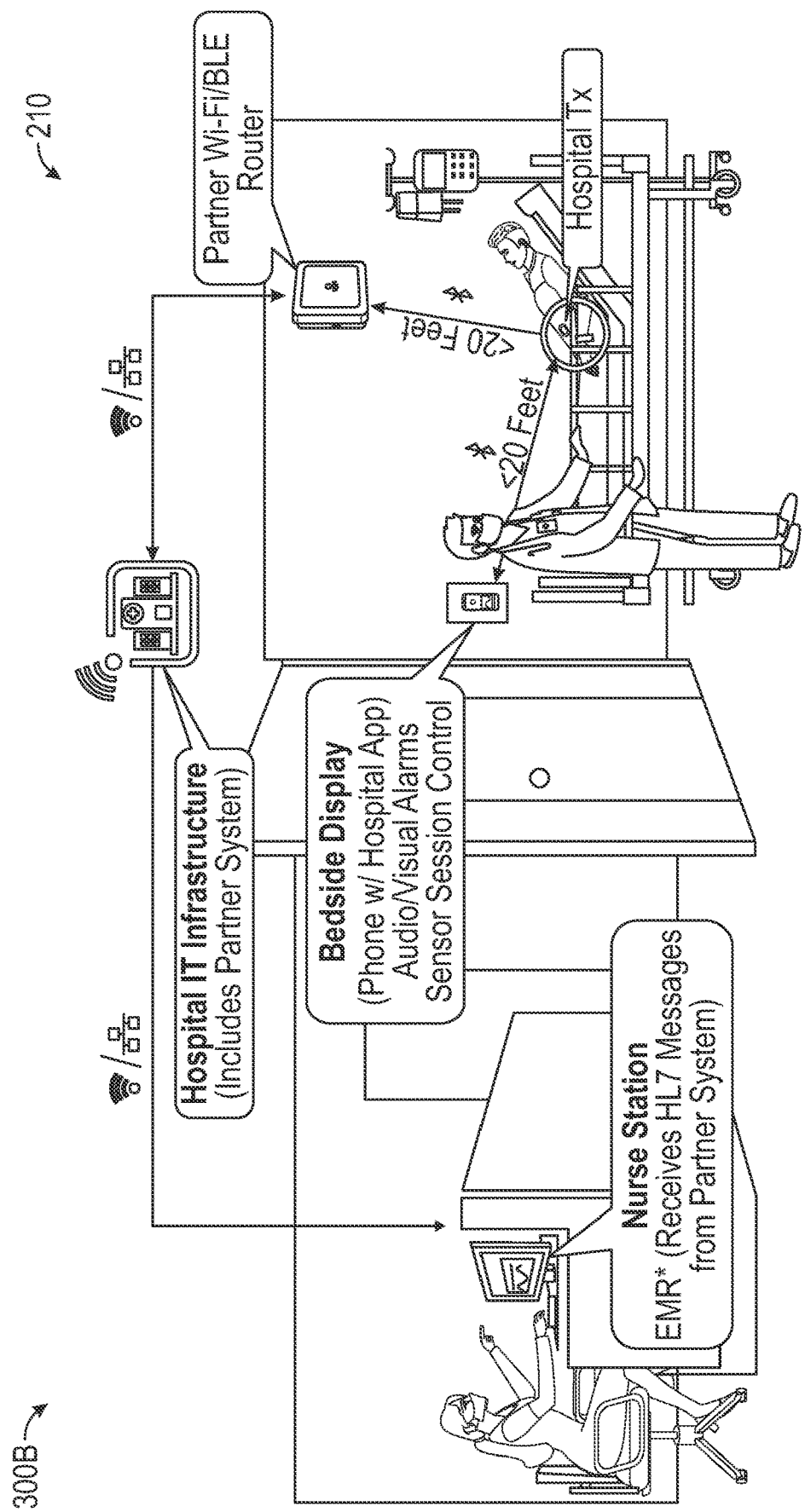
Figure 3C:
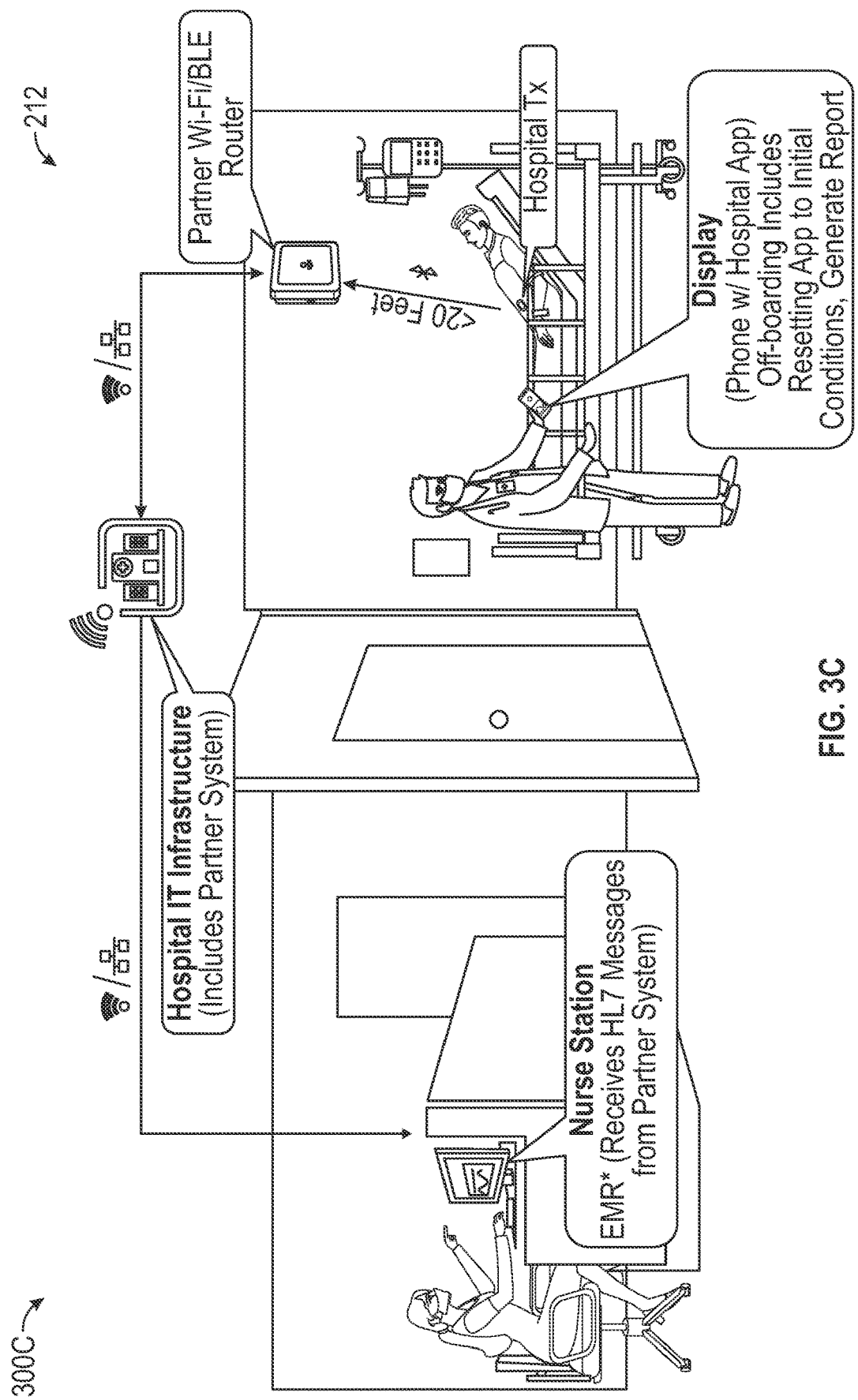
Figure 3C:
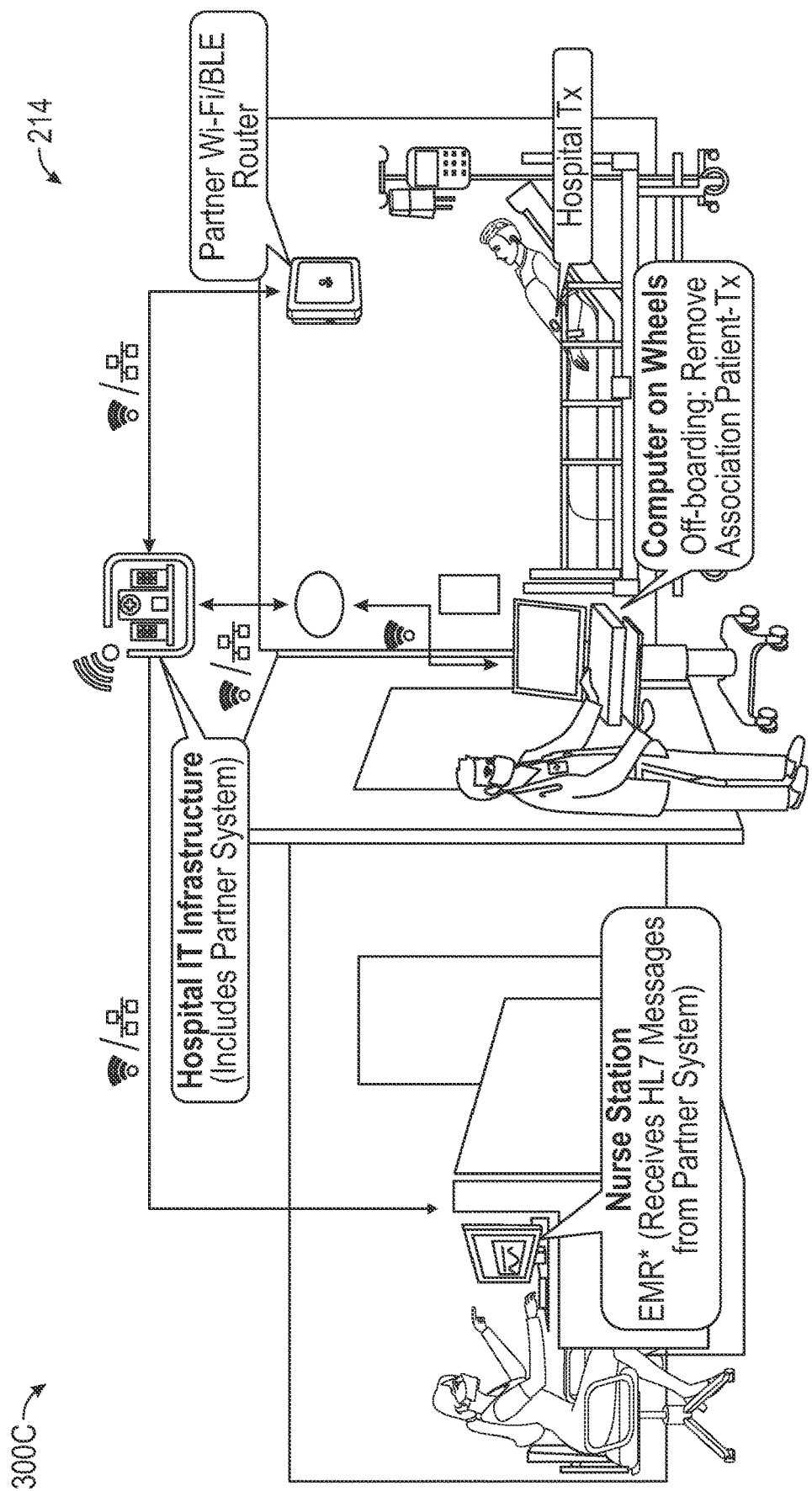
Figure 3C:
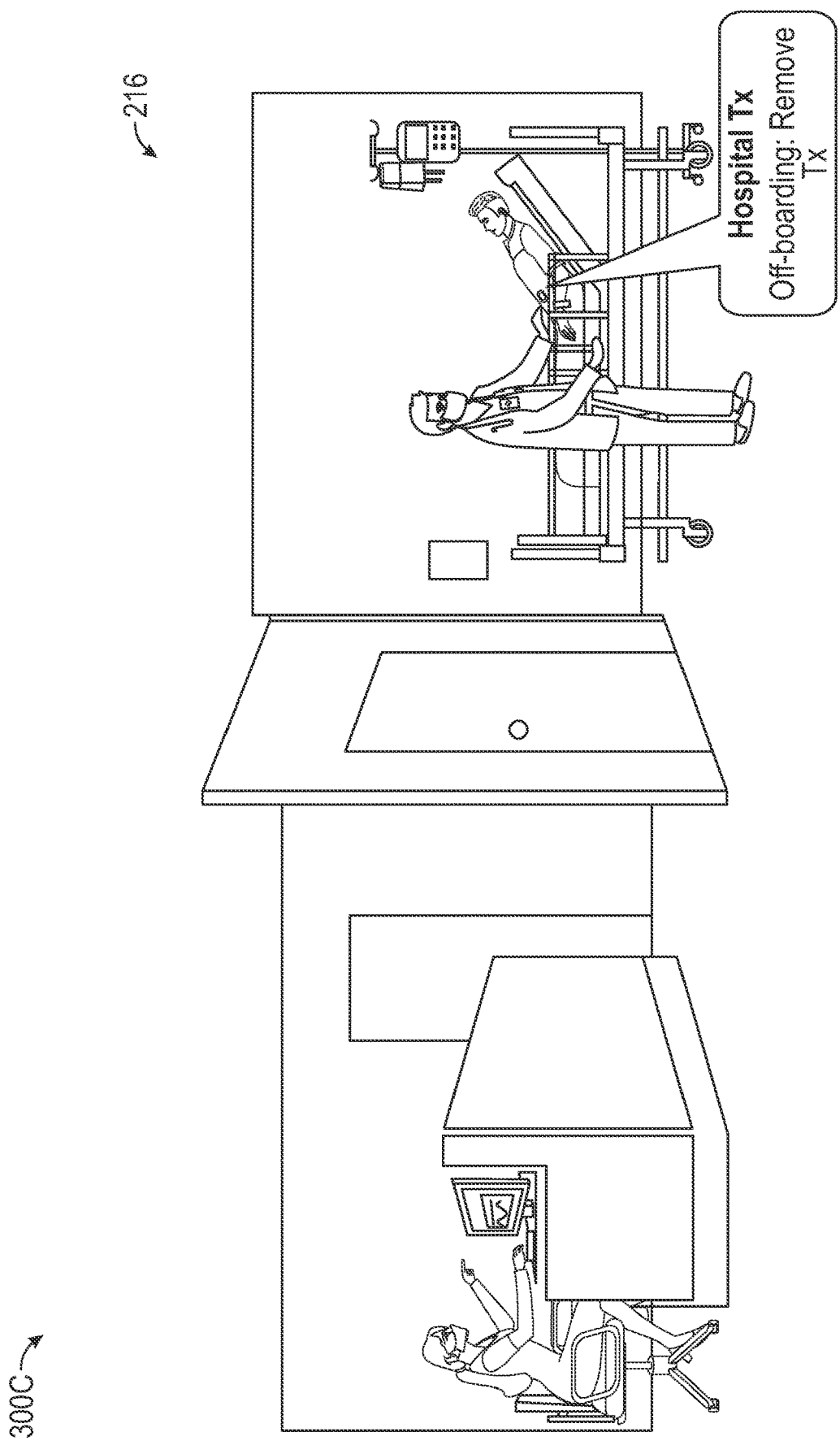

Streamlined procedures for on boarding and off boarding of these devices for every new patient use may be described with respect to FIGS. 2 and 3A-3C. In particular, FIG. 2 is a flow diagram illustrating example operations 200 for the on boarding and off boarding of devices in a healthcare facility, including establishing secure wireless connections between such devices, according to certain embodiments disclosed herein. Operations 200 of FIG. 2 may be explained in further detail with reference to FIGS. 3A-3C. In particular, FIGS. 3A-3C provide example illustrations of the operations described in FIG. 2 for the on boarding, regular use, and off boarding of devices in the healthcare facility, according to certain embodiments disclosed herein. While FIGS. 2 and 3A-3C may be described with respect to the admittance of a patient in a hospital setting, similar procedures may be used for the admittance of a patient in any other healthcare facility.

The hospitalization of a patient may include three phases: an admission period, an inpatient period, and a discharge period. During the admission period, onboarding operations 300A may be performed for the execution of certain security protocols to establish secure wireless communications between devices and SS 104. During the inpatient period, regular use operations 300B of such connected devices may be carried out for the discrete, continuous, and remote collection of one or more analyte measurements, such as glucose measurements of the patient, for inpatient monitoring. Lastly, during the discharge process, off boarding operations 300C may be performed to remove health information and other sensitive data stored on the device that is associated with the patient being discharged.

As shown in FIG. 2, on boarding operations 300A begin, at block 202, by providing the admitted patient with a patient identifier (ID) and preparing prescribed monitoring equipment including, at least, a bedside display application. The patient ID may be provided to a patient as a wristband. The patient ID wristband may contain a barcode, which may easily be scanned using a barcode scanner. The wristband provides important health care information about the patient, such as the patient's name, previous conditions, allergies, what type of medicine should be administered, medicine dosage, and the like. The prescribed monitoring equipment may include an electrocardiogram (ECG) monitor, a body temperature monitor, a pulse oximeter, capnography monitoring equipment, remote patient monitoring equipment, and the like. Preparing such equipment may include entering patient information into each of the devices (e.g., manually or by scanning the patient ID wristband), downloading one or more applications for use by the patient and/or a healthcare professional (HCP), placing equipment near the patient (e.g., less than 20 feet), etc. In certain embodiments, where SS 104 and mobile device 107*a* are deployed for use by a patient in the hospital, a hospital information technology (IT) professional, biomedical engineer, or the like may download a mobile health application, such as application 106 illustrated in FIG. 1A. For example, the hospital IT professional downloads application 106 from an application store (e.g., App Store) and initiates the set-up process.

At block 204, the patient may be provided with SS 104 for placement on the patient's body. For example, the HCP may prepare a site on the patient's skin for placement of a continuous analyte sensor, such as continuous analyte sensor 140 of SS 104. The HCP may then insert the continuous analyte senor 140 through the patient's skin and attach a transmitter to continuous analyte sensor 140. Once SS 104 is attached to the patient's body and activated, the set-up of a secure wireless connection (e.g., a secure BLE connection) between SS 104 and mobile device 107*a* may begin at block 206.

Setting up of a secure wireless communication may, in certain embodiments, begin by mobile device 107*a* and SS 104 engaging in a number of application layer identification and authentication protocols. In particular, based on instructions provided by application 106, the mobile device 107*a* may first attempt to identify SS 104 from potentially a number of different SSs in the vicinity. As a result, in certain embodiments, mobile device 107*a* and SS 104 may first engage in an identification protocol, thereby allowing mobile device 107*a* to securely identify the correct SS 104 to connect with. In one example, mobile device 107*a* may first obtain a transmitter ID associated with the transmitter of SS 104 (hereinafter referred to as "SSID"). For instance, in some embodiments, mobile device 107*a* may be equipped with a barcode scanner that is able to scan a QR code placed on or associated with SS 104. In some other embodiments, the SSID may be manually entered into mobile device 107*a* (e.g., by the patient, HCP, etc.). The QR code may indicate both the SSID as well as, in some cases, a pairing code. In other examples, one of many other techniques may instead be used to provide mobile device 107*a* with access to SSID.

Once mobile device 107*a* is in possession of SSID, it starts searching for the SS with the same SSID, based on a determination that the correct SS to connect with must have the same SSID. At the same time, SS 104 may be configured to advertise its SSID (e.g., all or a subset of the characters which make up the SSID) or some version thereof (e.g., a hash or an encrypted version) once SS 104 is activated. Note that in certain embodiments, if instead of mobile device 107*a*, SS 104 is engaging in wireless communications with a display device such as receiver 107*b*, SS 104 and receiver 107*b* may skip the identification phase. In such embodiments, the HCP may input the pairing code associated with SS 104 into a user interface provided by receiver 107*b* to allow the two devices to authenticate each other, as further described below.

For example, based on instructions provided by application 106, mobile device 107*a* may engage in or initiate a user-centric mutual authentication protocol at the application layer with SS 104. In certain embodiments, by engaging in the user-centric mutual authentication protocol, mobile device 107a and SS 104 are both configured to generate an authentication key (e.g., K-auth) based on a shared secret (e.g., pairing code, SSID, etc.). Examples of user-centric mutual authentication protocols are described in more detail herein and in U.S. application Ser. No. 17/308,754 which claims the benefit of U.S. Provisional Application Ser. No. 63/021,591 filed on May 7, 2020, which are incorporated herein by reference in their entireties.

The user-centric authentication protocol may include a key exchange algorithm, such as one of a variety of password authenticated key exchange (PAKE) algorithms. A passkey is then derived from the authentication key by both SS 104 and mobile device 107a to carry out an authenticated pairing protocol at a BLE layer of each of the devices. For example, at mobile device 107a and SS 104, the passkey is passed from the application layer to the BLE layer, where it is then used to achieve authenticated pairing with SS 104. Additional details regarding the authenticated paring process performed between mobile device 107a and SS 104 are provided below. Once a connection has been established between mobile device 107a and SS 104, the HCP may receive a confirmation message indicating BLE connection procedures are complete and have been successful.

Similar steps for establishing a secure wireless connection (e.g., secure BLE connection) between SS 104 and a partner system, such as partner system 110 illustrated in FIG. 1A, may be executed by both SS 104 and partner system 110. For example, in certain embodiments, the HCP may scan the SSID using a barcode scanner that is attached to a computer device, as shown in FIG. 3A, or manually enter the SSID into the computer device. The computer device may be communicating with partner system 110 through a Wi-Fi router (e.g., shown as BLE hub 108 in FIG. 1A and as Hospital Wi-Fi router in FIG. 3A). One or more software applications executing on the computer device may transmit the SSID to one or more software components executing at partner system 110 (e.g., described above with respect to FIG. 1A). In certain other embodiments, a mobile device may be used as an alternative to the computer device. The partner system 110 may then relay the received SSID to one or more BLE enabled routers placed in the patient's room (e.g., shown as Wi-Fi/BLE router 108 in FIG. 1A and as Partner Wi-Fi/BLE router in FIG. 3A). In certain embodiments, the one or more BLE enabled routers may use the received SSID to establish an initial connection between partner system 110 and SS 104. At the conclusion of the operations performed at block 206, the HCP may receive a confirmation message indicating BLE connection procedures are complete and have been successful between partner system 110 and SS 104.

On boarding operations 300A (e.g., operations of blocks 202-208) described above may be understood with reference to the illustrations provided in FIG. 3A.

Further, as shown in FIG. 2, regular use operations 300B begin subsequent to SS 104 establishing one or more secure connections with one or more entities in the healthcare facility. In particular, at block 210, the connected devices (e.g., SS 104, mobile device 107a, partner system 110, etc.) communicate using encrypted connections. In certain embodiments, communicating using an encrypted connection may include communicating one or more analyte measurements using an encrypted connection between SS 104 to mobile device 107a and/or partner system 110. In certain embodiments, analyte data for the patient may also be passed to an EMR, such as EMR system 112 illustrated in FIG. 1A, managed by the hospital and/or the caregiver facility.

Regular use operations 300B, and more specifically the operation at block 210, described above may be understood with reference to the illustration provided in FIG. 3B.

Hospital discharge describes the point at which inpatient hospital care ends, with ongoing care transferred to other primary, community, or domestic environments. Accordingly, at the completion of the inpatient hospital care of the patient, off boarding operations 300C may begin. Off boarding operations 300C begin at block 212 by an HCP resetting application 106 to its initial conditions. The reset of application 106 may include removing the SSID associated with the transmitter of SS 104, as well as any information related to the patient from application 106. In some cases, application 106 may be wiped from mobile device 107a. Similarly, at block 214, the HCP removes the SSID, as well as patient information associated with the discharged patient, from partner system 110 devices. At block 216, the off boarding process is completed by removing SS 104 from the patient for cleaning, disinfection, and sterilization. Although not illustrated, in some cases, off boarding operations 300C include generating a report for the patient prior to resetting application to its initial conditions at block 212.

Off boarding operations 300C (e.g., operations of blocks 212-216) described above may be understood with reference to the illustrations provided in FIG. 3C.

Operations 200 of FIG. 2 may be repeated each time a new patient is admitted to the hospital to establish secure connections between devices for the continuous monitoring of one or more analytes of the patient. Specifically, achieving security in each new setup, data cleaning/disinfecting, etc., for each new patient in the hospital setting may need to be considered when on boarding and off boarding devices, such as display device 107, are used for each new patient.

As discussed herein, SS 104 may pair with mobile device 107a, receiver 107b, and/or one or more other wired or wireless devices. Thus, while FIGS. 2 and 3A-3C illustrate only establishing a connection between SS 104 and mobile device 107a, in some other embodiments, similar steps may be followed to establish a connection between SS 104 and receiver 107b, where receiver 107b is deployed in the healthcare facility. However, unlike mobile device 107a, receiver 107b may not be capable of scanning a SSID of the patient for establishing an initial connection. Thus, instead, in some cases, the barcode scanner connected to the computer device may scan the SSID, and a configuration tool in the computer device may be used to configure receiver 107b with the SSID (as well as with other configured settings, including for example, threshold values for triggering alerts of the receiver 107b, etc.). In some other cases, the SSID may be input into receiver 107b by the HCP (and the configuration tool may be used to configure the other configured settings). Receiver 107b may follow operations similar to operations 200 for completing on boarding operations, and more specifically, achieving authenticated pairing with SS 104.

Authenticated Pairing With a No Input/No Output Device

Establishing a secure wireless connection between SS 104 and mobile device 107a, receiver 107b, and/or one or more other devices in healthcare facilities may involve engaging in identification, authentication, pairing, and/or bonding protocols or methods. Identification protocols may be designed, for example, to allow mobile device 107a and/or receiver 107b to effectively identify SS 104 while reducing the likelihood of an attacker being able to obtain any information during the identification process that may become useful in impersonating SS 104, mobile device 107a, and/or receiver 107b. Authentication protocols may be designed to allow each of SS 104, mobile device 107a, and/or receiver 107b to verify whether the other peer device is trusted by a user of the device and/or a root authority. Further, pairing and bonding protocols may be designed to allow for the exchange of information between SS 104, mobile device 107a, and/or receiver 107b to establish an encrypted connection for communication.

In certain embodiments, SS 104, mobile device 107a, and/or receiver 107b conform to one or more wireless protocols and standards (e.g., Bluetooth®, Bluetooth Low Energy (BLE), ANT protocols, Wi-Fi, Near Field Communication (NFC), etc.). For example, SS 104, mobile device 107a, and/or receiver 107b may be configured with Bluetooth related hardware and software for communication. Accordingly, SS 104, mobile device 107a, and/or receiver 107b may engage in identification, authentication, pairing, and/or bonding in accordance with the BLE standards.

As mentioned herein, BLE standards may require different protocols or methods of pairing for different levels of security defined by the BLE. The protocol used by devices for pairing may determine the strength of the authentication of the pairing which directly correlates to the level of security achieved by the devices. To achieve a highest level of security (e.g., Security Mode 1, Level 4 defined by the BLE), devices may be required to engage, at the BLE layer, in authenticated pairing involving a secure exchange of cryptographic keys, and in some cases, further engage in a key agreement protocol to generate a long term key (e.g., such as by using an Elliptic Curve Diffie-Hellman (EDCH) key agreement for LE secure connections). Devices that engage in authenticated pairing with LE-Secure protocols may achieve a higher level of security, as authenticated pairing facilities the protection of the communication from man-in-the-middle (MITM) attacks while LE secure protocols, such as ones involving EDCH, facilitate the protection of the communication from passive eavesdropping.

As such, according to certain embodiments described herein, SS 104, mobile device 107a, and receiver 107b may be configured to engage in authenticated pairing using a cryptographic key exchange protocol to achieve heightened security that is recommended in healthcare facilities (and, in some cases, further engage in EDCH after authenticated pairing has been achieved). In certain embodiments, SS 104, mobile device 107a, and receiver 107b may be configured to engage in an I/O-based pairing method, such as passkey entry pairing, in accordance with the BLE standards for authenticated pairing. However, I/O-based methods may not be feasible given SS 104 is designed as a no input/no output device. For example, as mentioned herein, to verify each bit of a passkey using an I/O-based pairing method, such as passkey entry pairing, the passkey must first be passed between the peer devices. Typically, in an I/O-based pairing method, a user views a passkey that is randomly generated and displayed at a first device with output/display capabilities and inputs the passkey into the second device with input/keyboard capabilities. Where one of the devices is not designed to have input and output capabilities, passing the passkey between devices for verification using an I/O-based pairing may not be possible.

Accordingly, embodiments of the present disclosure introduce methods for deriving a passkey at each of the peer devices for verification, thereby eliminating the need for both devices to have I/O capabilities. In particular, embodiments herein describe systems and methods for achieving authenticated pairing (e.g., recommended for improving security in the healthcare industry) using a passkey derived at the application layer at both devices. In some cases, the passkey derived at the application layer includes a passkey derived from K-auth generated as a result of executing a PAKE algorithm. Different embodiments may provide different methods for authenticated pairing based on the display device 107 that SS 104 is to be paired with. For example, in certain embodiments, methods for achieving authenticated pairing between SS 104 and a mobile device 107a having a first OS (e.g., a commercially available OS where passing of a passkey from the application layer to the BLE layer of mobile device 107a is not restricted) are provided. In certain embodiments, methods for achieving authenticated pairing between SS 104 and a mobile device 107a having a second OS (e.g., a commercially available OS where passing of a passkey from the application layer to the BLE layer of mobile device 107a is restricted) are provided. In certain embodiments, methods for achieving authenticated pairing between SS 104 and receiver 107b are provided.

Figure 4:
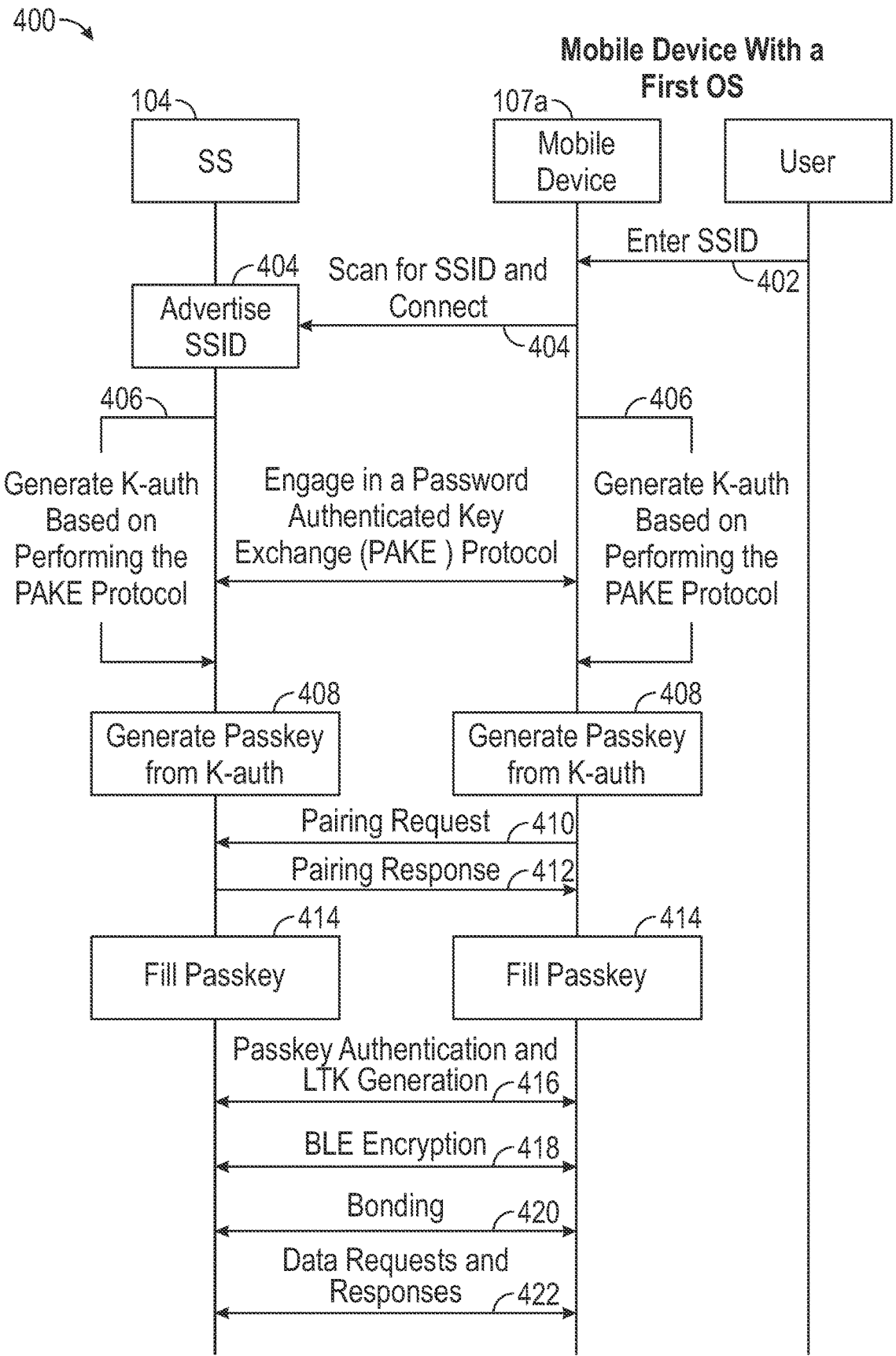
FIG. 4 is a call flow diagram illustrating the execution of certain security protocols to establish secure wireless communications between the analyte sensor system and a first mobile device, according to certain embodiments disclosed herein.

FIG. 4 is a call flow diagram 400 illustrating the execution of security protocols for the establishment of secure wireless communications between SS 104 and mobile device 107a having the first OS, according to certain embodiments disclosed herein. As mentioned, the first OS may be a commercially available OS where passing of a passkey from an application layer to a BLE layer of mobile device 107a is not restricted. As described in more detail below, the first OS executing on mobile device 107a may allow information, including the passkey, to be passed from the application layer to the BLE layer using an application programming interface (API) (e.g., a BLE API) provided by the OS to the application layer. While call flow diagram 400 illustrates the execution of security protocols for the establishment of secure wireless communications between SS 104 and mobile device 107a having the first OS, steps illustrated in call flow diagram 400 may be similarly followed when establishing secure wireless communication between SS 104 and one of a variety of other devices (e.g., a router, a hub, or any other computing device) with an OS similar or identical to the first OS.

In certain embodiments, the transmitter of SS 104 is configured with an SSID as well as a pairing code. In certain cases, the SSID and pairing code may be indicated (e.g., printed or located) on SS 104 itself or a package thereof. In certain embodiments, a pairing code refers to a Bluetooth pairing code that may be used later for authentication between mobile device 107a and SS 104 as well as the actual pairing between the two devices. In certain embodiments, instead of a pairing code, another code or password may be used.

As shown at step 402 in FIG. 4, once a user obtains the SSID and pairing code, the user provides the SSID and the pairing code as an input into a mobile health application, such as application 106, executing on mobile device 107a during the set-up process. Alternatively, the user may use mobile device 107a, which may be equipped with an image scanner, to scan a bar code or QR code placed on SS 104 itself or a package thereof. The bar code or QR code may indicate the SSID as well as the pairing code. In certain other embodiments, one of many other techniques may be used for providing mobile device 107a with access to the SSID and the pairing code.

Having received the SSID, mobile device 107a, at step 404, starts scanning for an SS with the same SSID. At the same time SS 104 may be configured to advertise, at step 404, its SSID after the user places SS 104 on their body and activates a transmitter of SS 104. It is noted that, in some cases, the advertised SSID may include a modified or a derived version of the SSID.

Mobile device 107a may then compare the SSID obtained by mobile device 107a (e.g., from the user, through scanning a bar/QR code, etc.), at step 402, with the SSID advertised by SS 104 at step 404. If the obtained SSID and the advertised SSID are the same, mobile device 107a identifies that SS 104, which advertised the SSID at step 404, is the correct SS to connect with.

As shown in FIG. 4, once mobile device 107a identifies SS 104 as the correct SS to connect with, SS 104 and mobile device 107a may be configured to authenticate each other using one or more authentication protocols. For example, SS 104 and mobile device 107a may engage in a user-centric mutual authentication protocol. A user-centric mutual authentication protocol, allows each of SS 104 and mobile device 107a to generate K-auth based on a shared secret (e.g., the pairing code). In certain embodiments, K-auth is an advanced encryption standard (AES) key. If both mobile device 107a and SS 104 generate the same K-auth then SS 104 and mobile device 107a are able to conclude that the other is in possession of the shared secret and, therefore, trusted by the user.

The user-centric authentication protocol may include one of a variety of PAKE algorithms. A distinguishing feature of PAKE is that one device (e.g., SS 104) is able to authenticate itself to the other device (e.g., mobile device 107a) using a password or shared secret (e.g., pairing code) such that an unauthorized party (one who controls the communication channel but does not possess the password) cannot participate in the method and is constrained as much as possible from brute-force guessing of the password. If an attacker engages in a PAKE protocol with a device, the attacker is only able to make a single guess of the shared secret and, further, will only learn that its guess was incorrect. No other information is leaked.

One of a variety of PAKE algorithms may be used as part of the user-centric authentication protocol. Examples include Juggling PAKE or J-PAKE, EC-J-PAKE (elliptic curve cryptography), SPEKE (simple password exponential key exchange), CRS-J-PAKE (common reference string-J-PAKE), AuCPace (Augmented Composable Password Authenticated Connection Establishment), BSPEKE (a "B" extension for SPEKE), zkPAKE (zero-knowledge PAKE), C2C-PAKE (client to client PAKE), and EKE (encrypted key exchange).

In certain embodiments, as shown at step 406 in FIG. 4, SS 104 and mobile device 107a generate K-auth based on performing the PAKE protocol. Mobile device 107a may be configured via application 106 running on mobile device 107a to perform the PAKE protocol. After performing PAKE, both devices are in possession of the same K-auth.

In certain embodiments, K-auth derived during PAKE may be used to generate a passkey at SS 104 and mobile device 107a. Generating a passkey based on K-auth may include creating a passkey that is different from but based on K-auth (e.g., by hashing or encrypting K-auth) or using K-auth itself as the passkey. As described in more detail below, generation of the passkey from K-auth may remove the need to have two devices with I/O capabilities to achieve authenticated pairing using an I/O-based pairing method, such as the passkey entry pairing method. Accordingly, at step 408, SS 104 and mobile device 107a may generate the passkey at the application layer based on K-auth. Mobile device 107a may be configured by application 106 to generate the passkey from K-auth.

At step 410, subsequent to generating the passkey, SS 104 and mobile device 107a may begin pairing. Pairing is performed to establish keys which can then be used to encrypt a link. In general, there are three phases for paring in LE secure connections pairing: phase 1 for pairing feature exchange, phase 2 for key generation method selection and authentication, and phase 3 for long term key (LTK) generation.

During pairing phase 1, security features that include, for example, I/O capabilities, requirements for MITM protection, etc., are exchanged between devices. The exchange of such security features may be via a pairing request and pairing response packet. Accordingly, to begin pairing between SS 104 and mobile device 107a, at step 410, mobile device 107a is configured (per its BLE configuration) to transmit a pairing request to SS 104. The pairing request may identify I/O capabilities of mobile device 107a, as well as an indication of what I/O capabilities mobile device 107a is requesting SS 104 have. In response to the pairing request from mobile device 107a, at step 412, SS 104 may transmit a pairing response to mobile device 107a with the security features it supports.

While the example embodiment of FIG. 4 illustrates mobile device 107a, at step 410, transmitting a pairing request to SS 104 and, at step 412, SS 104 responding to the pairing request, in certain other embodiments, the pairing request may be transmitted by SS 104 to mobile device 107a, and mobile device 107a may be configured to respond to the pairing request received from SS 104.

The combination of supported features among SS 104 and mobile device 107a may determine what pairing model(s) may be used to generate the encryption keys in pairing phase 2. In particular, different pairing models may require that different conditions are met prior to using the method for pairing. For example, to perform an I/O-based pairing method such as passkey entry pairing, at least one peer device needs to be designed with an input capability to enter a passkey, and the other peer device needs to be designed with a display capability for displaying a passkey.

Thus, performing passkey entry pairing for SS 104, which has neither input nor output capabilities, is a technical challenge. However, to overcome this technical challenge, aspects described herein provide techniques for circumventing such I/O capability requirements. In particular, according to certain aspects, SS 104 may be configured to report fake I/O capabilities in its pairing response, transmitted at step 412, to trigger execution of the passkey entry pairing protocol. For example, in certain embodiments, SS 104 may be configured to report a fake output/display capability to mobile device 107a, thereby causing mobile device 107a to skip generating a random passkey, as it may be configured to do (per its BLE configuration) when a peer device reports input-only capabilities or no capabilities. More particularly, instead of disclosing its real capabilities (e.g., no I/O capabilities), SS 104 may be configured to report to mobile device 107a that SS 104 has output/display capabilities at step 412. As a result, in response, mobile device 107a does not generate a random six-digit passkey for pairing. Instead, mobile device 107a is tricked into assuming that SS 104 is going to generate and display the passkey. Tricking mobile device 107a in this manner allows for the passkey that was generated at the application layer on mobile device 107a (e.g., at step 408) to be used by mobile device 107a to perform the passkey entry pairing protocol, as further described below.

Phase 2, e.g., authentication, of the passkey entry pairing protocol may be performed at the BLE layer of each of SS 104 and mobile device 107a; thus, the passkey generated at the application layer of each of SS 104 and mobile device 107a at step 408 may need to be communicated to the BLE layer prior to execution of phase 2 of the passkey entry pairing protocol. SS 104, which is a proprietary system, can be configured by the manufacturer to pass an application layer passkey from the application layer to the BLE layer. However, passing an application layer passkey from the application layer to the BLE layer at a mobile device 107a that executes a commercially available OS may be a technical challenge depending on the type of OS used by mobile device 107a.

In some cases, as described in relation to FIG. 4, mobile device 107a may execute an OS that allows information to be passed from the application layer to the BLE layer using an API provided by the OS to the application layer. In such cases, the passkey derived from K-auth at the application layer of mobile device 107a is passed to the BLE layer using the API exposed to the application layer. In other words, the passkey is sent directly to the BLE layer from application 106 running on mobile device 107a. This may be accomplished without user interaction and/or any pop-up dialogs.

In some other cases, mobile device 107a is configured with an OS that does not allow the passkey to be passed to the BLE layer. In such cases, to overcome this technical challenge, certain embodiments herein involve techniques for utilizing user interaction for passing the passkey derived from K-auth at the application layer to the BLE layer. In particular, in certain embodiments, a user of mobile device 107a may be required to enter the passkey in a pop-up dialog of mobile device 107a. This case may be described in more detail below with respect to call flow diagram 500 of FIG. 5.

Because the example embodiment described in FIG. 4 describes pairing between SS 104 and mobile device 107a with an OS which does not restrict the passing of the passkey from the application layer to the BLE layer, at step 414, mobile device 107a may fill the passkey, or in other words, use an API to send the passkey directly to the BLE layer. Similarly, at step 414, SS 104 may be programed to transmit the passkey generated at step 408 to a BLE layer of SS 104.

At step 416, SS 104 and mobile device 107a may engage in an authentication process to verify each bit of the passkey. The authentication process is a method of gradual disclosure (e.g., between SS 104 and mobile device 107a) of each bit of the passkey until all bits of the passkey have been verified. Assuming all bits of the passkey maintained at SS 104 match all bits of the passkey maintained at mobile device 107a, then authentication may be deemed successful. However, in cases where the passkeys do not match, the pairing aborts. Generally, such a mismatch indicates an attacker has intercepted the communication between SS 104 and mobile device 107a. Alternatively, in a case where a user is prompted to enter a passkey into the device, as described below with respect to call flow diagram 500 of FIG. 5, a mismatch may indicate the user has entered an incorrect key in the pop-up dialog. In this case, mobile device 107a may be configured to indicate to a user that the passkey entered is incorrect. Assuming the passkeys match, further at step 416, SS 104 and mobile device 107a may execute phase three of the passkey entry pairing protocol and compute an LTK. In certain embodiments, the LTK is a 128-bit key used to generate the contributory session key for an encrypted connection.

In certain embodiments, the session key is any encryption key used to symmetrically encrypt only one communication session between SS 104 and mobile device 107a. In other words, the session key is a temporary key that is only used once, during one stretch of time, for encrypting and decrypting data; whereas, future communication between the two parties would be encrypted with different session keys. Thus, at step 418, the session key may be used to encrypt the connection between the two devices.

At step 420, SS 104 and mobile device 107a engage in bonding. In some examples, SS 104 and mobile device 107a may store additional information about each other during the bonding process. For example, after the encryption of the connection at step 418, SS 104 and mobile device 107a bond by exchanging the LTK and storing the LTK for later use. In other words, bonding refers to the creation of permanent security between SS 104 and mobile device 107a.

After pairing and bonding, SS 104 and mobile device 107a are ready to exchange data over a secure connection. For example, SS 104 may encrypt data (e.g., at the BLE layer), including analyte measurements associated with the user, for transmission to mobile device 107a at step 422. Mobile device 107a may similarly encrypt data for transmission to SS 104.

At a later time (not shown in FIG. 4) after communication between SS 104 and mobile device 107a is complete, SS 104 and mobile device 107a may disconnect. For example, in certain embodiments, for power saving purposes, SS 104 may periodically exchange data with mobile device 107a (e.g., by switching between a sleep mode and an operational mode periodically). For example, in certain embodiments, SS 104 may "wake up" every few minutes (e.g., five minutes) to exchange data with mobile device 107a but go into a sleep mode in-between the five minute intervals. Each time SS 104 "wakes up", SS 104 and mobile device 107a may perform security protocols for re-establishing a secure wireless connection between the two devices. Security protocols for re-establishing a secure wireless connection between the two devices may include all or only certain steps of the operations illustrated in FIG. 4. In some cases, the type of connection (e.g., always connected, reconnect after every five minute interval, etc.) between the two devices may determine which protocols are needed for re-establishing the secure wireless connection.

Further details regarding identification, authentication, pairing, and/or bonding described with respect to FIG. 4 can be found in the various specifications of such technologies (e.g., Bluetooth specification), which is incorporated herein by reference in its entirety. The specifications may be provided by the governing bodies of such technologies.

Note that some of the steps illustrated in FIG. 4 may be performed in a different order than illustrated in FIG. 4 or may be performed in parallel or overlap in time. Accordingly, the reference numbers assigned to the different steps illustrated in FIG. 4 may not be indicative of the order in which they are performed in certain embodiments.

As mentioned herein, in some cases, SS 104 may establish a wireless connection with a mobile device 107a with an OS which restricts passing of the passkey from the application layer to the BLE layer (e.g., a mobile device 107a having a different OS (i.e., a second OS) than mobile device 107a illustrated in FIG. 4). Accordingly, FIG. 5 is a call flow diagram 500 illustrating the execution of security protocols for establishing secure wireless communications between SS 104 and mobile device 107*a* having a second OS (e.g., where passing of a passkey from the application layer to the BLE layer of the mobile device 107*a* is restricted), according to certain embodiments disclosed herein. While call flow diagram 500 illustrates the execution of security protocols for the establishment of secure wireless communications between SS 104 and mobile device 107*a* having the second OS, steps illustrated in call flow diagram 500 may be similarly followed when establishing secure wireless communication between SS 104 and one of a variety of other devices (e.g., a router, a hub, or any other computing device) with an OS similar or identical to the second OS.

Figure 5:
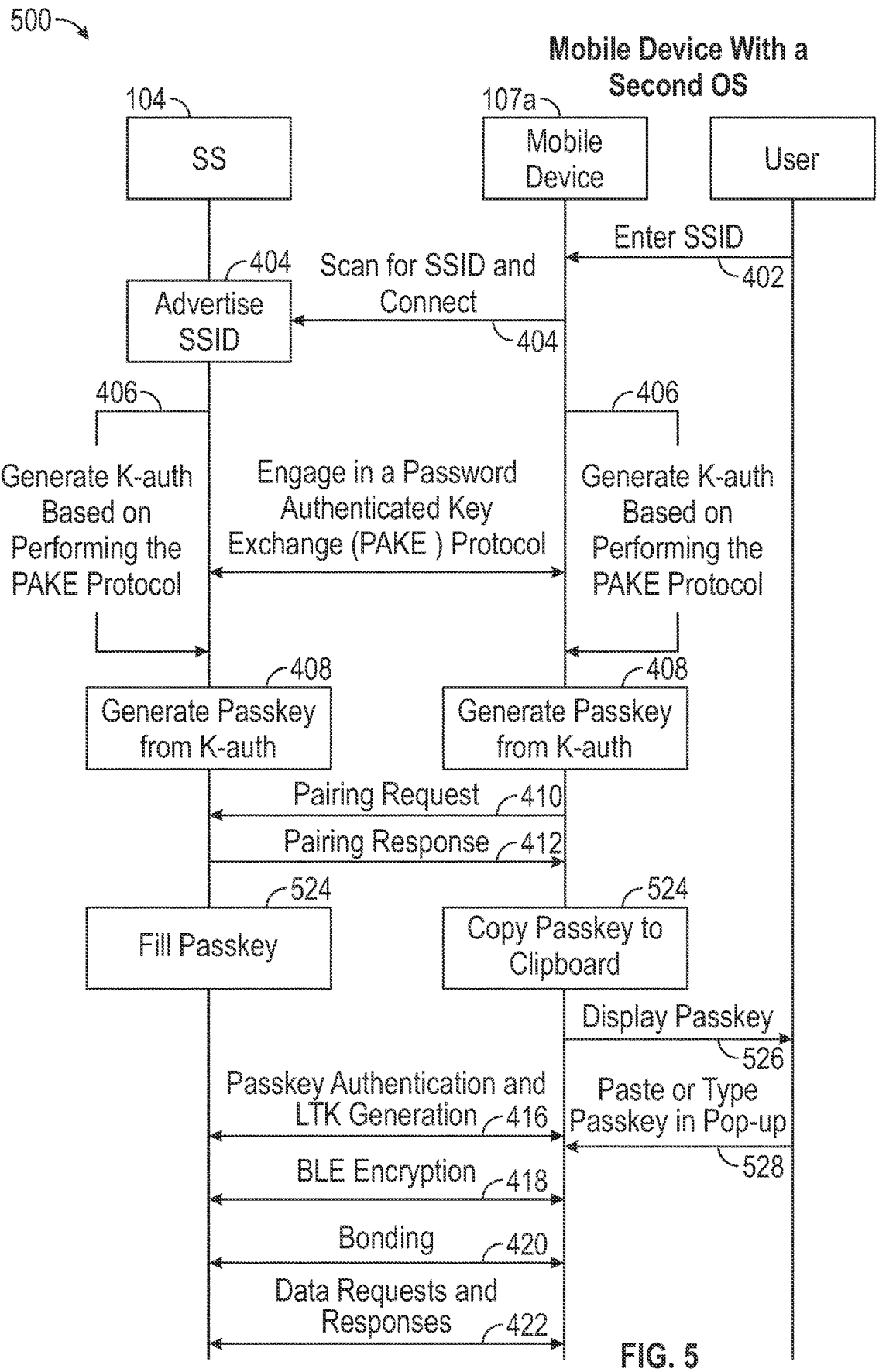
FIG. 5 is a call flow diagram illustrating the execution of certain security protocols to establish secure wireless communications between the analyte sensor system and a second mobile device, according to certain embodiments disclosed herein.

Steps 402-412 of FIG. 5 may be similar to steps 402-412 described with respect to FIG. 4. However, in contrast to FIG. 4, after the pairing response (e.g., indicating a fake display/output capability of the transmitter) is transmitted at step 412, and passkey entry pairing is selected as the method for authentication, mobile device 107*a* may be configured to automatically copy the passkey generated at step 408 to a clipboard. Mobile device 107*a* may be configured via application 106 running on mobile device 107*a* to automatically copy the passkey (e.g., a six-digit decimal number) to the clipboard. As used herein, a clipboard refers to a temporary buffer designed to hold data contents for cut-copy-paste operations. When data is moved in the OS environment of mobile device 107*a*, the data is stored in the clipboard. Generally, the clipboard's contents are temporary and reside in the random access memory (RAM) of mobile device 107*a*. Although FIG. 5 illustrates the passkey being copied to the clipboard at step 524 after the pairing request and pairing response packets are transmitted at steps 410 and 412, respectively, in some cases, the passkey is copied to the clipboard prior to mobile device 107*a* transmitting the pairing request at step 410.

At step 526, the passkey copied to the clipboard of mobile device 107*a* may be displayed to the user. For example, the passkey may be displayed in a UI of mobile device 107*a* for viewing (and in some cases, copying by the user). In some cases, at step 528, the user copies the displayed passkey and pastes it in a pop-up dialogue or window. In certain embodiments, the pop-up dialogue is generated in response to a user of mobile device 107*a* selecting SS 104 as a device to pair with mobile device 107*a*. For example, the user may select SS 104 from a list of detected Bluetooth devices that may be paired with mobile device 107*a*. After selection of SS 104 from the list of detected devices, the pop-up dialogue may be generated for input of the passkey by the user.

Once the passkey is entered into the pop-up dialogue, the passkey is communicated to the BLE layer. In some other cases, the user may prefer to type the passkey instead of pasting the passkey. Accordingly, in some cases, at step 528, the user types the displayed passkey in a pop-up dialogue displayed by mobile device 107*a*. As such, the pop-up dialogue may be designed to allow for a user to paste the passkey and/or type the passkey. Once the passkey is entered into the pop-up dialogue, the passkey is communicated to the BLE layer. Similar to step 414 of FIG. 4, at step 524 of FIG. 5, SS 104 is also programmed to transmit the passkey generated at step 408 to the BLE layer.

Remaining steps 416-422 of FIG. 5 are similar to steps 416-422 of FIG. 4 to establish a secure wireless communication between SS 104 and mobile device 107*a*. Further, similar to FIG. 4, steps illustrated in FIG. 5 may be performed in a different order than illustrated in FIG. 5 or may be performed in parallel or overlap in time. Accordingly, the reference numbers assigned to the different steps illustrated in FIG. 4 may not be indicative of the order in which they are performed in certain embodiments.

In certain embodiments, where SS 104 is pairing with a proprietary receiver, such as receiver 107*b* illustrated in FIGS. 1A and 1B, the two devices may also engage in authentication, pairing, and bonding protocols, similar to those described above with respect to FIGS. 4 and 5. However, unlike FIGS. 4 and 5, when SS 104 is pairing with receiver 107*b*, SS 104 may be configured to report to receiver 107*b* that SS 104 has input/keyboard capabilities instead of disclosing its real capabilities (e.g., no I/O capabilities). Accordingly, receiver 107*b* may be prompted to generate a passkey for display to SS 104. However, instead of generating a random passkey for pairing with SS 104, receiver 107*b* may be programmed to derive the passkey from K-auth. Receiver 107*b* may further be programmed to allow for passing of the passkey to the BLE layer without any API (e.g., different from FIG. 4 where the passkey is passed to the BLE layer via an API) or user interaction (e.g., different from FIG. 5 where the passkey is passed to the BLE layer via user interaction), where the passkey is then used for authentication.

SS 104 may be configured to report different fake capabilities when establishing a connection with mobile device 107*a* than when establishing a connection with receiver 107*b* such that, in cases where SS 104 is pairing with both mobile device 107*a* and receiver 107*b* at the same time, SS 104 may be able to distinguish between the two connections or pairing processes. In particular, when two or more devices are trying to pair simultaneously with SS 104, there may be no way to separate the interaction between the devices. Accordingly, different fake capabilities are reported by SS 104 for pairing with mobile device 107*a* and receiver 107*b* to distinguish between (1) interactions between SS 104 and mobile device 107*a* and (2) interactions between SS 104 and receiver 107*b*. In certain embodiments, distinguishing between the two types of connections is advantageous for identifying devices were the pairing process is not controlled by an application or the application layer (e.g. commercially available mobile devices, devices running a real-time operating system (RTOS), etc.). Note that a device that is not in control of the pairing process at the application layer may ask the transmitter to initiate the pairing process.

It is noted that where the transmitter pairs with one or more other devices (e.g., such as partner system 110 illustrated in FIG. 1A), not including a proprietary or embedded receiver, similar methods described with respect to pairing between SS 104 and a mobile device 107*a* described above with respect to FIGS. 4 and 5 may be used to establish a secure wireless connection.

Co-Located Application Attacks

In certain embodiments, achieving heightened security among devices deployed in the healthcare facility may require solving two vulnerabilities: (1) passive eavesdropping or MITM attacks and (2) co-located application attacks (e.g., unauthorized applications co-located on a BLE device accessing pairing-protected data from the BLE device). Authenticated pairing, e.g., using the methods described above, provides sufficient MITM protection for current vulnerabilities. In some examples, co-located application attack vulnerability may also exist.

Co-located application attacks may be of concern where SS 104 pairs with mobile device 107*a*, as opposed to receiver 107*b*. For example, receiver 107*b* may be considered to be a dedicated receiver where no additional applications may be installed thereon. Accordingly, receiver 107b, where deployed, may not be vulnerable to co-located application attacks. On the other hand, however, mobile devices 107a may execute multiple applications.

Thus, in certain embodiments where SS 104 pairs with a mobile device 107a, in order to minimize the co-located application attack vulnerability, mobile device 107a may be configured to apply a Principle of Least Privilege. The Principle of Least Privilege states that a subject should be given only those privileges needed for it to complete its task. Accordingly, the Principle of Least Privilege implemented by mobile device 107a may limit privileges of other applications executing on mobile device 107a (excluding application 106 described above with respect to FIG. 1A) to protect from co-location application attacks (e.g., other applications are given the bare minimum privileges necessary to perform its function).

Each of these non-limiting examples can stand on its own or can be combined in various permutations or combinations with one or more of the other examples. The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round", a component that is not precisely circular (e.g., one that is slightly oblong or is a many-sided polygon) is still encompassed by this description.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A method of facilitating secure communications between a display device and a sensor system for measuring analyte levels, comprising:

executing, at an application layer of the display device, a password authenticated key exchange (PAKE) protocol with the sensor system to derive an authentication key;

executing, at the display device, an authenticated pairing protocol with the sensor system, wherein the executing of the authenticated pairing protocol comprises:

receiving, at the display device from the sensor system, an indication of a first input/output (I/O) capability, wherein the sensor system is not configured with the first I/O capability;

obtaining a passkey that is derived from the authentication key at the application layer of the display device; and authenticating the sensor system by verifying that the passkey matches another passkey generated at the sensor system, wherein the other passkey is derived by the sensor system from executing the PAKE protocol at an application layer of the sensor system;

after the authenticating is successful, establishing an encrypted connection between the display device and the sensor system; and receiving, at the display device from the sensor system, analyte data indicative of measured analyte levels via the encrypted connection.

2. The method of claim 1, wherein establishing the encrypted connection between the display device and the sensor system comprises:
   computing, at a Bluetooth Low Energy (BLE) layer of the display device, a long term key (LTK) used to generate a session key;
   establishing, by the display device, an encrypted channel with the sensor system using the session key; and
   executing, at the display device, a bonding procedure with the sensor system.

3. The method of claim 1, further comprising:
   transmitting, to the sensor system, a request to initiate pairing with the sensor system, wherein the indication of the first I/O capability received at the display device, is transmitted by the sensor system in response to the request.

4. The method of claim 1, wherein the display device is a mobile device with a mobile operating system (OS), and the first I/O capability indicated by the sensor system comprises an output capability, wherein the sensor system is not configured with the output capability, and wherein the indication of the output capability prompts the mobile device to refrain from generating a random passkey.

5. The method of claim 4, wherein the mobile OS of the mobile device obtains, at a Bluetooth Low Energy (BLE) layer of the mobile device, the passkey using a BLE application programming interface (API), and wherein the passkey is derived by the mobile device by executing the PAKE protocol at the application layer.

6. The method of claim 4, wherein obtaining the passkey that is derived from the authentication key at the application layer of the display device comprises:
   displaying the passkey to a user of the mobile device; and
   displaying a pop-up dialogue on a user interface of the mobile device to receive the passkey as user input, wherein the mobile device is configured to pass the passkey received as user input at the application layer to a Bluetooth Low Energy (BLE) layer of the mobile device.

7. The method of claim 6, wherein the passkey is received as the user input by the user:
   copying the passkey displayed at the mobile device and pasting the passkey in the pop-up dialogue; or
   typing the passkey displayed at the mobile device into the pop-up dialogue.

8. The method of claim 4, wherein the mobile device is configured to have multiple applications executing thereon and is further configured with a principle of least privilege to provide only privileges that are needed to execute an application used for receiving the analyte data from the sensor system.

9. The method of claim 1, wherein the display device is a receiver, and the first I/O capability indicated by the sensor system comprises an input capability, wherein the sensor system is not configured with the input capability.

10. The method of claim 9, wherein the receiver is configured to obtain, at a Bluetooth Low Energy (BLE) layer of the receiver, the passkey derived from executing the PAKE protocol at the application layer of the receiver.

11. The method of claim 9, wherein the receiver is configured to have only one application executing thereon for receiving the analyte data.

12. The method of claim 1, wherein the passkey that is derived from the authentication key:
   comprises the authentication key derived from executing the PAKE protocol; or
   is derived from the authentication key derived from executing the PAKE protocol.

13. A method of facilitating secure communications between a sensor system for measuring analyte levels and a display device, comprising:
   executing, at an application layer of the sensor system, a password authenticated key exchange (PAKE) protocol with the display device to derive an authentication key;
   executing, at the sensor system, an authenticated pairing protocol with the display device, wherein the executing of the authenticated pairing protocol comprises:
      transmitting, from the sensor system to the display device, an indication of a first input/output (I/O) capability, wherein the sensor system is not configured with the first I/O capability;
      obtaining a passkey that is derived from the authentication key at the application layer of the sensor system; and
      authenticating the sensor system by verifying that the passkey matches another passkey generated at the display device, wherein the other passkey is derived by the display device from executing the PAKE protocol at an application layer of the display device;
   after the authenticating is successful, establishing an encrypted connection between the sensor system and the display device; and
   transmitting, from the sensor system to the display device, analyte data indicative of measured analyte levels via the encrypted connection.

14. The method of claim 13, wherein establishing the encrypted connection between the display device and the sensor system comprises:
   computing, at the sensor system, a long term key (LTK) used to generate a session key;
   establishing, at the sensor system, an encrypted channel with the display device using the session key; and
   executing, at the sensor system, a bonding procedure with the display device.

15. The method of claim 13, further comprising:
   receiving, from the display device, a request to initiate pairing with the display device, wherein the indication of the first I/O capability transmitted, from the sensor system to the display device, is transmitted in response to the request.

16. The method of claim 13, wherein the display device is a mobile device with a mobile operating system (OS), and the first I/O capability indicated by the sensor system comprises an output capability, wherein the sensor system is not configured with the output capability, and wherein the indication of the output capability prompts the mobile device to refrain from generating a random passkey.

17. The method of claim 13, wherein the display device is a receiver, and the first I/O capability indicated by the sensor system comprises an input capability, wherein the sensor system is not configured with the input capability.

18. The method of claim 13, wherein the sensor system is pre-configured to obtain, at a Bluetooth Low Energy (BLE) layer of the sensor system, the passkey derived from executing the PAKE protocol at the application layer of the sensor system.

19. The method of claim 13, wherein the passkey derived from the authentication key:
   comprises the authentication key derived from executing the PAKE protocol; or
   is from the authentication key derived from executing the PAKE protocol.

20. A sensor system comprising:
an analyte sensor operable to generate analyte measurements; and
a sensor electronics module comprising:
  a memory comprising executable instructions; and
  a processor in data communication with the memory and configured to execute the instructions to cause the sensor system to:
    execute, at an application layer of the sensor system, a password authenticated key exchange (PAKE) protocol with a display device to derive an authentication key;
    execute, at the sensor system, an authenticated pairing protocol with the display device, wherein the processor being configured to execute the authenticated pairing protocol comprises the processor being configured to:
      transmit, from the sensor system to the display device, an indication of a first input/output (I/O) capability, wherein the sensor system is not configured with the first I/O capability;
      obtain a passkey that is derived from the authentication key at the application layer of the sensor system; and
      authenticate the sensor system by verifying that the passkey matches another passkey generated at the display device, wherein the other passkey is derived by the display device from executing the PAKE protocol at an application layer of the display device;
    after the authenticating is successful, establish an encrypted connection between the sensor system and the display device; and
    transmit, from the sensor system to the display device, analyte data indicative of the analyte measurements via the encrypted connection.

21. The sensor system of claim 20, wherein the processor being configured to establish the encrypted connection between the display device and the sensor system comprises the processor being configured to:
  compute, at the sensor system, a long term key (LTK) used to generate a session key;
  establish, at the sensor system, an encrypted channel with the display device using the session key; and
  execute, at the sensor system, a bonding procedure with the display device.

22. The sensor system of claim 20, wherein the processor is further configured to:
  receive, from the display device, a request to initiate pairing with the display device, wherein the indication of the first I/O capability transmitted, from the sensor system to the display device, is transmitted in response to the request.

23. The sensor system of claim 20, wherein the display device is a mobile device with a mobile operating system (OS), and the first I/O capability indicated by the sensor system comprises an output capability, wherein the sensor system is not configured with the output capability, and wherein the indication of the output capability prompts the mobile device to refrain from generating a random passkey.

24. The sensor system of claim 20, wherein the display device is a receiver, and the first I/O capability indicated by the sensor system comprises an input capability, wherein the sensor system is not configured with the input capability.

25. The sensor system of claim 20, wherein the sensor system is pre-configured to obtain, at a Bluetooth Low Energy (BLE) layer of the sensor system, the passkey derived from executing the PAKE protocol at the application layer of the sensor system.

26. The sensor system of claim 20, wherein the passkey derived from the authentication key:
  comprises the authentication key derived from executing the PAKE protocol; or
  is derived from the authentication key derived from executing the PAKE protocol.

* * * * *